US010613075B2

(12) United States Patent
Kimura et al.

(10) Patent No.: US 10,613,075 B2
(45) Date of Patent: Apr. 7, 2020

(54) SCREENING APPARATUS AND SCREENING METHOD

(71) Applicant: Furukawa Electric Co., Ltd., Tokyo (JP)

(72) Inventors: Kenichi Kimura, Tokyo (JP); Jie Xu, Tokyo (JP); Ken Tsukii, Tokyo (JP); Toru Takahashi, Tokyo (JP); Mariko Matsunaga, Tokyo (JP)

(73) Assignee: Furukawa Electric Co., Ltd., Tokyo (JP)

( * ) Notice: Subject to any disclaimer, the term of this patent is extended or adjusted under 35 U.S.C. 154(b) by 413 days.

(21) Appl. No.: 15/256,997

(22) Filed: Sep. 6, 2016

(65) Prior Publication Data

US 2016/0370342 A1   Dec. 22, 2016

Related U.S. Application Data

(63) Continuation of application No. PCT/JP2015/055277, filed on Feb. 24, 2015.

(30) Foreign Application Priority Data

Mar. 7, 2014  (JP) ................................. 2014-044914

(51) Int. Cl.
*G01N 1/00* (2006.01)
*G01N 33/487* (2006.01)
(Continued)

(52) U.S. Cl.
CPC ............. *G01N 33/487* (2013.01); *G01N 1/14* (2013.01); *G01N 15/1463* (2013.01);
(Continued)

(58) Field of Classification Search
CPC ....................................................... G01N 1/00
See application file for complete search history.

(56) References Cited

U.S. PATENT DOCUMENTS

2002/0094533 A1* 7/2002 Hess .................... B01J 19/0046
                                                              435/6.14
2006/0269446 A1* 11/2006 Gilbert .............. B01L 3/502761
                                                              422/400

FOREIGN PATENT DOCUMENTS

JP      2003-116518       4/2003
JP      2006-187206       7/2006
(Continued)

OTHER PUBLICATIONS

Written Opinion dated May 19, 2015 in PCT/JP2015/055277, filed Feb. 24, 2015 (previously filed, submitting English translation only).

(Continued)

*Primary Examiner* — Jyoti Nagpual
(74) *Attorney, Agent, or Firm* — Oblon, McClelland, Maier & Neustadt, L.L.P.

(57) ABSTRACT

A screening apparatus for searching for a predetermined microparticle based on optical information emitted from microparticles to selectively pick up the microparticle searched for includes a measurement chip that is made of a light permeable material, the measurement chip having a well formed therein that retains a liquid including at least one microparticle, a measuring section that is configured to acquire optical information emitted by the microparticles retained in the measurement chip, an analyzing section that is configured to analyze the optical information to extract optical information associated with the microparticles retained in the well, a liquid retaining section provided on the measurement chip, a draining section that is configured to drain a liquid retained in the liquid retaining section, an introducing section that introduces a liquid into the liquid retained section, and a liquid level controlling section that controls a liquid level of the liquid retaining section.

17 Claims, 20 Drawing Sheets

(51) Int. Cl.
  *G01N 15/14*  (2006.01)
  *G01N 21/64*  (2006.01)
  *G01N 21/76*  (2006.01)
  *G01N 1/14*  (2006.01)
  *G01N 15/10*  (2006.01)
  *G01N 35/10*  (2006.01)
  *G01N 15/00*  (2006.01)

(52) U.S. Cl.
  CPC ..... *G01N 21/6428* (2013.01); *G01N 21/6452* (2013.01); *G01N 21/76* (2013.01); *G01N 15/1434* (2013.01); *G01N 2015/0065* (2013.01); *G01N 2015/1006* (2013.01); *G01N 2035/1025* (2013.01); *G01N 2201/061* (2013.01); *G01N 2201/068* (2013.01)

(56) References Cited

FOREIGN PATENT DOCUMENTS

| | | |
|---|---|---|
| JP | 4002720 | 11/2007 |
| JP | 2008-136415 | 6/2008 |
| JP | 4117341 | 7/2008 |
| JP | 2010-85343 | 4/2010 |
| JP | 2010-88347 | 4/2010 |
| WO | WO 2014/097991 A1 | 6/2014 |

OTHER PUBLICATIONS

English translation of the International Preliminary Report on Patentability dated Sep. 13, 2016 in PCT/JP2015/055277.
International Search Report dated May 19, 2015 in PCT/JP2015/055277, filed Feb. 24, 2015 (with English Translation).
Written Opinion dated May 19, 2015 in PCT/JP2015/055277, filed Feb. 24, 2015.
Japanese Office Action dated Nov. 2, 2015 in Japanese Application 2015-531370 (with English Translation).
Japanese Office Action dated Feb. 15, 2016 in Japanese Application 2015-531370 (with English Translation).
Decision to Grant dated May 16, 2016 in Japanese Application 2015-531370 (with English Translation).
Combined Office Action and Search Report dated Nov. 28, 2018 in Chinese Patent Application No. 201580011975.7 (with partial unedited computer generated English translation).
Chinese Office Action dated Mar. 25, 2019 in Patent Application No. 201580011975.7, 8 pages (with unedited computer generated English translation).
Notification to Grant Patent Right for Invention dated Sep. 4, 2019 in the corresponding CN application No. 201580011975.7.

\* cited by examiner

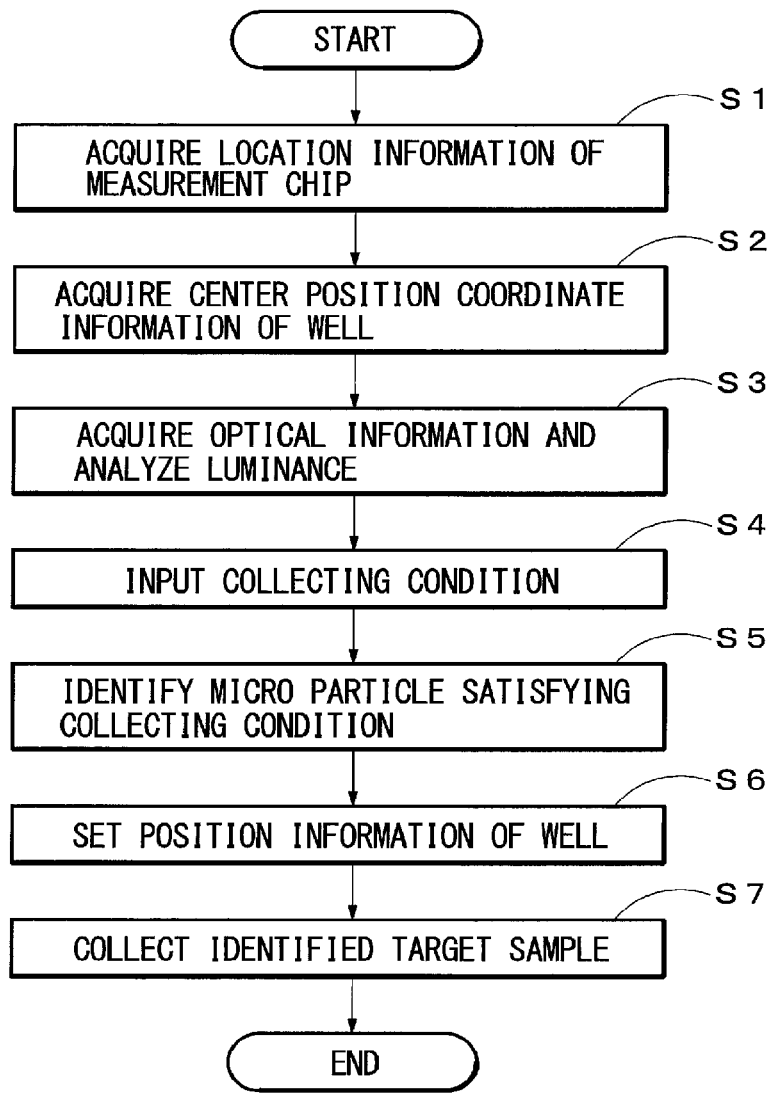
F I G. 6

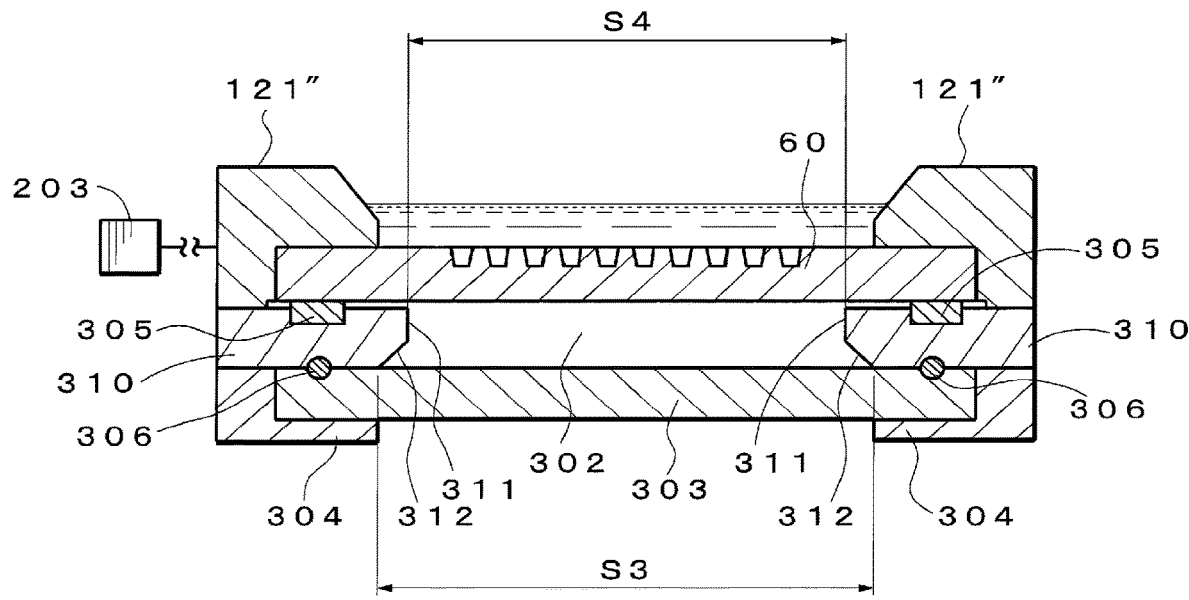
F I G. 18 A
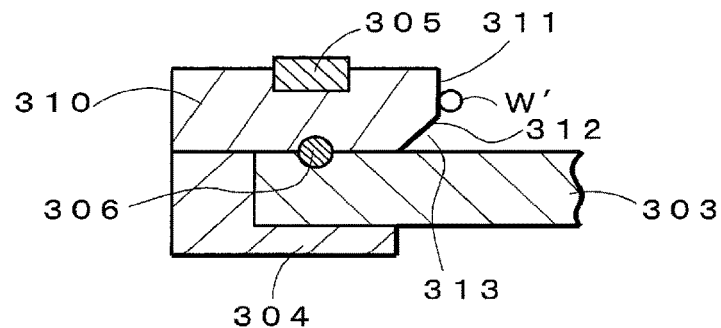
F I G. 18 B
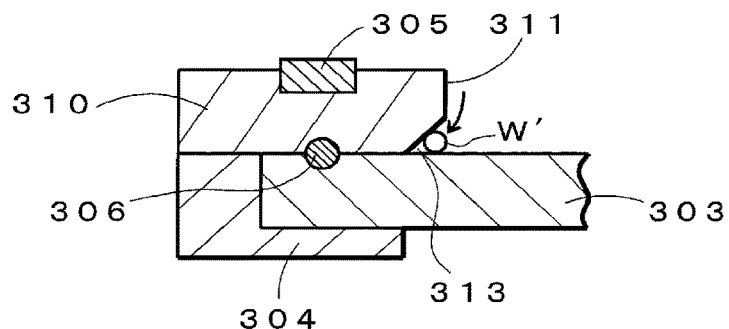
F I G. 18 C

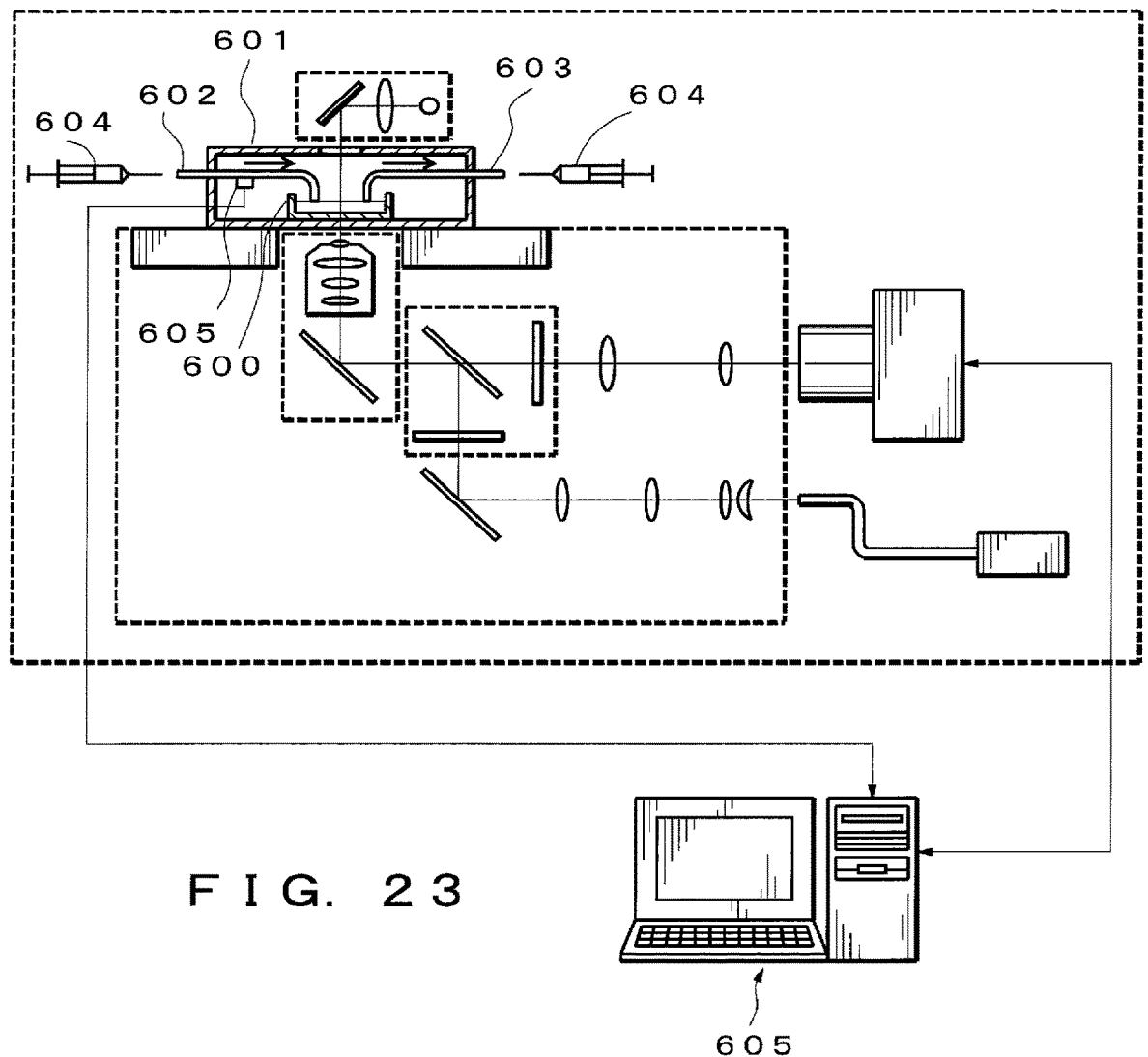
F I G. 2 3

SCREENING APPARATUS AND SCREENING METHOD

CROSS REFERENCE TO RELATED APPLICATIONS

This is a continuation application of International Patent Application No. PCT/JP2015/055277 filed Feb. 24, 2015, which claims the benefit of Japanese Patent Application No. 2014-044914, filed Mar. 7, 2014, the full contents of all of which are hereby incorporated by reference in their entirety.

BACKGROUND

Technical Field

The present disclosure relates to a screening apparatus and a screening method for illuminating microparticle, such as cells, detecting a microparticle to be a target sample based on fluorescence emitted from the microparticle, and selectively sucking and collecting the relevant microparticle.

Background Art

In the related art, microparticle screening apparatuses are widely used as apparatuses for identifying and sorting microscopic samples, such as cells, in research and testing in the medical field. Recently, in research and testing organizations, there is a need for obtaining identifying and sorting processes of the samples without fracture and for increasing efficiency of research and testing by performing those processes more accurately. Particularly, in a certain field, due to an increasing need for performing the identifying and sorting on a cell-by-cell basis, there is also a need for increasing accuracy and efficiency in the identifying and sorting processes on a cell-by-cell basis.

FIG. 21 is a schematic diagram showing a culture chamber of the related art for culturing cells used as samples. A culture chamber 400 has a two layered structure including a cell culture room 401 disposed at an upper layer and a warm water circulation room 402 disposed at a lower layer.

At the cell culture room 401, which is disposed at an upper layer, a cover glass 403 for culturing cells M' is secured to a cover glass securing unit 404 and a closed space 405 is formed between the cover glass 403 and an optical glass, described below, of the warm water circulation room 402. The cover glass securing unit 404 is provided with culture liquid changing ports 406 through which a cell culture liquid in the second closed space 405 can be changed.

At the warm water circulation room 402, which is disposed at a lower layer, two pieces of optical glass 407, 407 are disposed to oppose each other and secured to an optical glass securing unit 408. Between these two pieces of optical glass, a closed region 409 for circulating warm water is formed. Further, the optical glass securing unit 408 is provided with a warm water inlet 410 through which warm water flows into the closed region 409 and a warm water outlet 411 through which warm water flows out from the closed region 409.

With the culture chamber of the related art, a culture liquid in the closed region 405 can be changed through the culture liquid changing ports 406, and the temperature of the culture liquid can be controlled by performing PID control of the temperature of warm water in the warm water circulation room 402 in accordance with the measured temperature of the culture liquid in the closed region 405 (e.g., see Japanese Patent No. 4117341).

FIG. 22 is a cross sectional view showing another culture vessel of the related art. A culture vessel 500 is adhered and secured to a substrate 502 with adhesive seal 501 such as silicon seal. A culture liquid is accumulated in a liquid exchange unit 500A of the culture vessel 500 through a tube 503. The new culture liquid accumulated in the liquid exchange unit 500A is changed with the old culture liquid in the cell culture section 504 through a semipermeable membrane 505, and the old culture liquid is drawn out through a tube 506. With this configuration, it is also possible to change the culture liquid in the culture vessel 500 and in the cell culture section 504 through the tubes 503 and 506 (e.g., see Japanese Patent No. 4002720).

FIG. 23 is a drawing showing yet another culture vessel of the related art. A chamber 601 in which a culture vessel 600 is accommodated is provided with two glass tubes 602 and 603. Each of the glass tubes 602 and 603 penetrates through a side wall of the chamber 601 and is fixed to the chamber 601. One end of each of the glass tubes 602 and 603 is immersed into a culture medium in the culture vessel 600.

When giving a drug stimulus to culture cells in the culture vessel 600, the user makes use of a pipette 604 (or a syringe) to discharge the culture medium through the glass tube 603 and immediately after this, a drug is injected into the glass tube 602. A dosage sensor 605 comprising a pressure sensor is attached to a surface of the glass tube 602, and as the drug passes through the glass tube 602, a signal in response to timing of the passage is transmitted to a computer 605.

With this configuration, the culture medium in the culture vessel 600 can be discharged through the glass tube 603 and a drug can be injected into the culture vessel 600 through the glass tube 602. Also, with the dosage sensor 605, presence or absence of dosing or timing of dosing can be monitored (e.g., see Japanese Laid-Open Patent Publication No. 2008-136415).

However, with the culture chamber of the related art shown in FIG. 21, when replacing a culture medium in the closed region with a new culture medium, a new culture medium mixes with an old culture medium and thus a new culture medium and an old culture medium cannot be accurately replaced. With the culture vessel shown of the related art in FIG. 22, since an old culture medium in the cell culture section 404 is replaced with a new culture medium through the semipermeable membrane 405, similarly to the technique of FIG. 21, a new culture medium and an old culture medium cannot be accurately replaced and a long time is required for replacement.

Further, with the culture vessel of the related art shown in FIG. 23, since a culture medium is discharged from a culture vessel, and immediately after, a drug is injected into the culture vessel using a pipette or a syringe, it is not possible to replace the culture medium and the drug accurately, and also, it is inefficient.

Particularly, in a case where a reagent is introduced into one of the culture chambers or the culture vessels described above, the reagent will be diluted due to the mixing of the reagent and the culture medium in the vessel. When it is attempted to perform sorting using as little reagent as possible for saving resources and costs, there is a problem that an emission intensity of the target sample becomes weak, and sorting accuracy decreases.

The present disclosure is related to providing a screening apparatus and a screening method that can accurately and efficiently replace a liquid in a vessel retaining microparticles, and can improve sorting accuracy.

SUMMARY

According to a first aspect of the present disclosure, a screening apparatus for searching for a predetermined microparticle based on optical information emitted from microparticles to selectively pick up the microparticle searched for includes a measurement chip that is made of a light permeable material, the measurement chip having a well formed therein that retains a liquid including at least one microparticle, a measuring section that is configured to acquire optical information emitted by the microparticles retained in the measurement chip, an analyzing section that is configured to analyze the optical information to extract optical information associated with the microparticles retained in the well, a liquid retaining section provided on the measurement chip, a draining section that is configured to drain a liquid retained in the liquid retaining section, an introducing section that introduces a liquid into the liquid retained section, and a liquid level controlling section that controls a liquid level of the liquid retaining section.

According to a second aspect of the present disclosure, a screening apparatus for searching for a predetermined microparticle based on optical information emitted from microparticles to selectively pick up the microparticle searched for includes a measurement chip that is made of a light permeable material, the measurement chip having a well formed therein that retains a liquid including at least one microparticle, a measuring section that is configured to acquire optical information emitted by the microparticles retained in the measurement chip, an analyzing section that is configured to analyze the optical information to extract optical information associated with the microparticles retained in the well, and a temperature controlling section configured to control a temperature of the measurement chip and/or the receiving plate.

According to a third aspect of the present disclosure, a screening method for searching for a predetermined microparticle based on optical information emitted from microparticles to selectively pick up the microparticle searched for includes a first measuring step including introducing a reference liquid on the measurement chip, measuring position coordinate information of a well in the measurement chip, and thereafter draining the reference liquid, a second measuring step including introducing a liquid for searching on the measurement chip and measuring optical information emitted by microparticles in the well, a cleaning step including draining the liquid for searching on the measurement chip, introducing and draining the reference liquid for at least once to clean the measurement chip, an identifying step of identifying a microparticle which satisfied a predetermined collecting condition as a target sample based on the position coordinate information and the optical information thus measured, a collecting step of collecting the target sample, and a liquid level controlling step of controlling a liquid level on the measurement chip, the liquid level controlling step being at least in the second measurement step among the first measurement step, the second measurement step and the cleaning step.

According to the present disclosure, since the liquid level of the liquid retaining section formed on the measurement chip is controlled, a liquid in wells configured to receive microparticles and a liquid retaining section can be replaced accurately and efficiently during each step of sorting. Therefore, optical information of the microparticles in the well can be acquired accurately and a sorting accuracy can be improved.

Also, since an amount and a draining timing of a liquid drained from the liquid retaining section and an amount and an introducing timing of a liquid introduced into the liquid retaining section can be controlled individually, the liquid level of the liquid retaining section can be changed to a desired level and optical information of the microparticle in the well can be acquired more accurately.

Particularly, by keeping the liquid surface of a reference liquid on the measurement chip at a stable position, the state at which microparticles are not reacting can be measured accurately. Also, by lowering the liquid level of the reference liquid to a predetermined liquid level when replacing the reference liquid such as a medium with a liquid for search such as a reagent solution, dilution of the liquid for search which is introduced afterwards can be suppressed, and the natural reaction of a microparticle that is to be a target sample can be obtained accurately. Further, emission intensity of the microparticles can be improved with a little amount of liquid for search. Further, when the liquid surface of the liquid for search is low, the liquid level varies in the vicinity of the securing member of the liquid retaining section due to an influence such as surface tension, but by keeping the liquid level of the liquid for search at a predetermined level during reaction of the microparticles, the state of microparticles during reaction can be measured accurately at all positions on the measurement chip. Further, by draining almost all liquid for search on the measurement chip and thereafter introducing and draining the reference liquid, accuracy and efficiency of the cleaning of the measurement chip can be improved.

Further, according to the present disclosure, since a gas is blown on a face on the side opposite to a face on which the well of the measurement chip is provided, even in a case where the reference liquid and liquid for search are maintained at a predetermined temperature for keeping microparticles such as cells in an optimum condition depending on the purpose, condensation does not occur on a face of the measurement chip. Therefore, refraction and scattering of light due to condensation can be prevented, and optical information of the microparticles can be acquired accurately.

Also, since the temperature of the measurement chip and/or the receiving plate is controlled, cells can be activated or made dormant, and cells can be kept in an optimum condition depending on the purpose.

BRIEF DESCRIPTION OF DRAWINGS

FIG. 6 is a flow chart for explaining a method of screening a target sample in the present disclosure.

FIG. 18A is an overall cross sectional view a variant of the securing member shown in FIG. 17. FIGS. 18B and 18C are partial cross sectional views for explaining how water droplets are collected.

FIG. 23 is a cross sectional view showing yet another culture vessel of the related art.

DETAILED DESCRIPTION

Further features of the present disclosure will become apparent from the following detailed description of exemplary embodiments with reference to the accompanying drawings.

Figure 1:
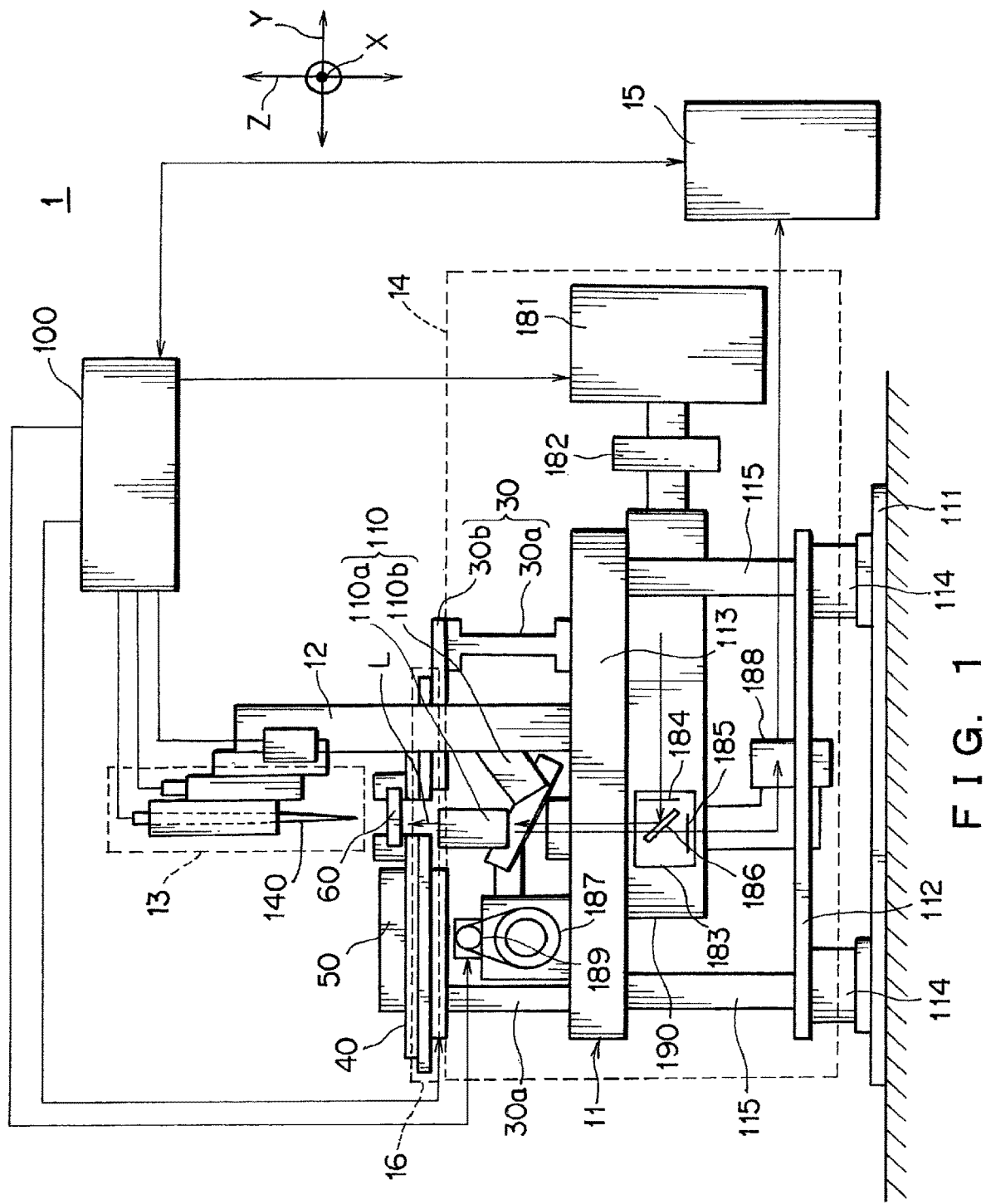
FIG. 1 is a side view schematically showing a configuration of a screening apparatus of an embodiment of the present disclosure.
Figure 2:
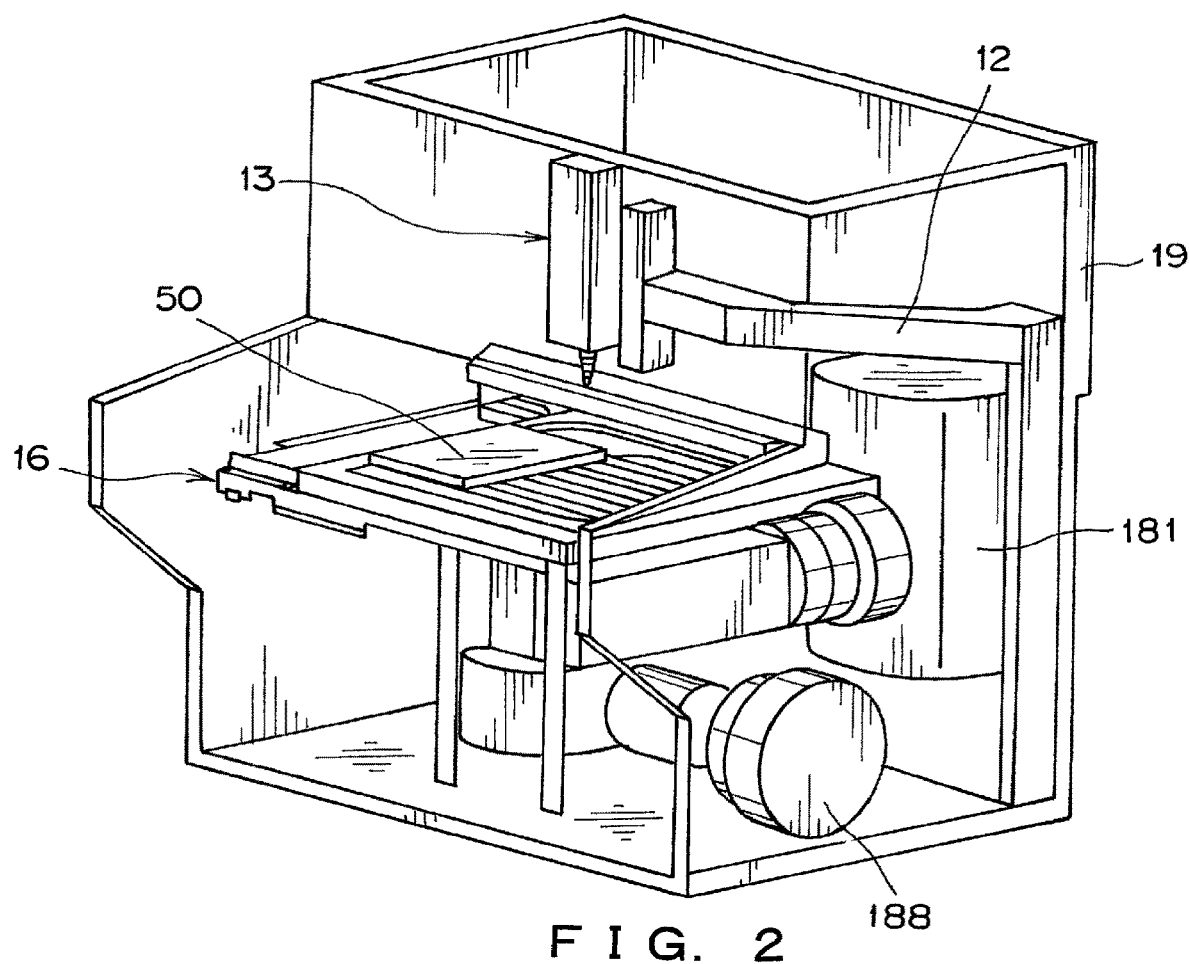
FIG. 2 is a perspective view of the screening apparatus of FIG. 1.

FIG. 1 is a side view schematically showing a configuration of a screening apparatus of an embodiment of the present disclosure, and FIG. 2 is a perspective view of the screening apparatus of FIG. 1.

In FIGS. 1 and 2, a screening apparatus 1 is an apparatus that searches for a predetermined microparticle to be a target sample based on fluorescence emitted from a plurality of microparticles (e.g., living cells) on a measurement chip 60, and selectively sucks microparticles in a well in which a microparticle satisfying collecting conditions is retained to collect them onto a receiving plate 50.

Specifically, the screening apparatus 1 includes a base 11, a supporting section 12 (FIG. 2), a collecting section 13, a measuring section 14, an image analyzing section 15 (analyzing section) and a moving section 16, and, as shown in FIG. 2, all the sections are covered with a cover 19. The cover 19 prevents entry of light and foreign substances from outside. The base 11 is a main body frame for holding each component of the screening apparatus 1.

As shown in FIG. 1, a direction perpendicular to the plane of paper of FIG. 1 is an X-direction (first direction) and a right and left direction is a Y-direction (second direction). Z-direction is a direction perpendicular to the X-direction and the Y-direction.

The base 11 includes plate-like members 111, 112 and 113 disposed substantially horizontally, and holds the collecting section 13, the measuring section 14 and the moving section 16 via the plate-like members. The plate-like members 111 and 112 are secured parallel to each other by a plurality of vertical members 114, and the plate-like members 112 and 113 are secured parallel to each other by a plurality of members 115. The vertical member 114 is made of a material having a vibration shielding property and is adjustable in height.

The supporting section 12 and a supporting table 30 are secured on the plate-like member 113, which is located at the top most position among the plurality of plate-like members. The supporting section 12 is disposed upright on the plate-like member 113 vertically and along Z-direction. The supporting table 30 includes leg sections 30a and a support-plate 30b. The plate-like members 111, 112 and 113 and the support-plate 30b are disposed at a predetermined interval between each other in the Z-direction.

The moving section 16 is mounted and secured on the support-plate 30b of the supporting table 30. A mounting table 40, a receiving plate 50 and a measurement chip 60 are mounted on the moving section 16. The moving section 16 is capable of moving and positioning the mounting table 40, i.e., the receiving plate 50 and the measurement chip 60, along the X-direction and/or the Y-direction.

Figure 3:
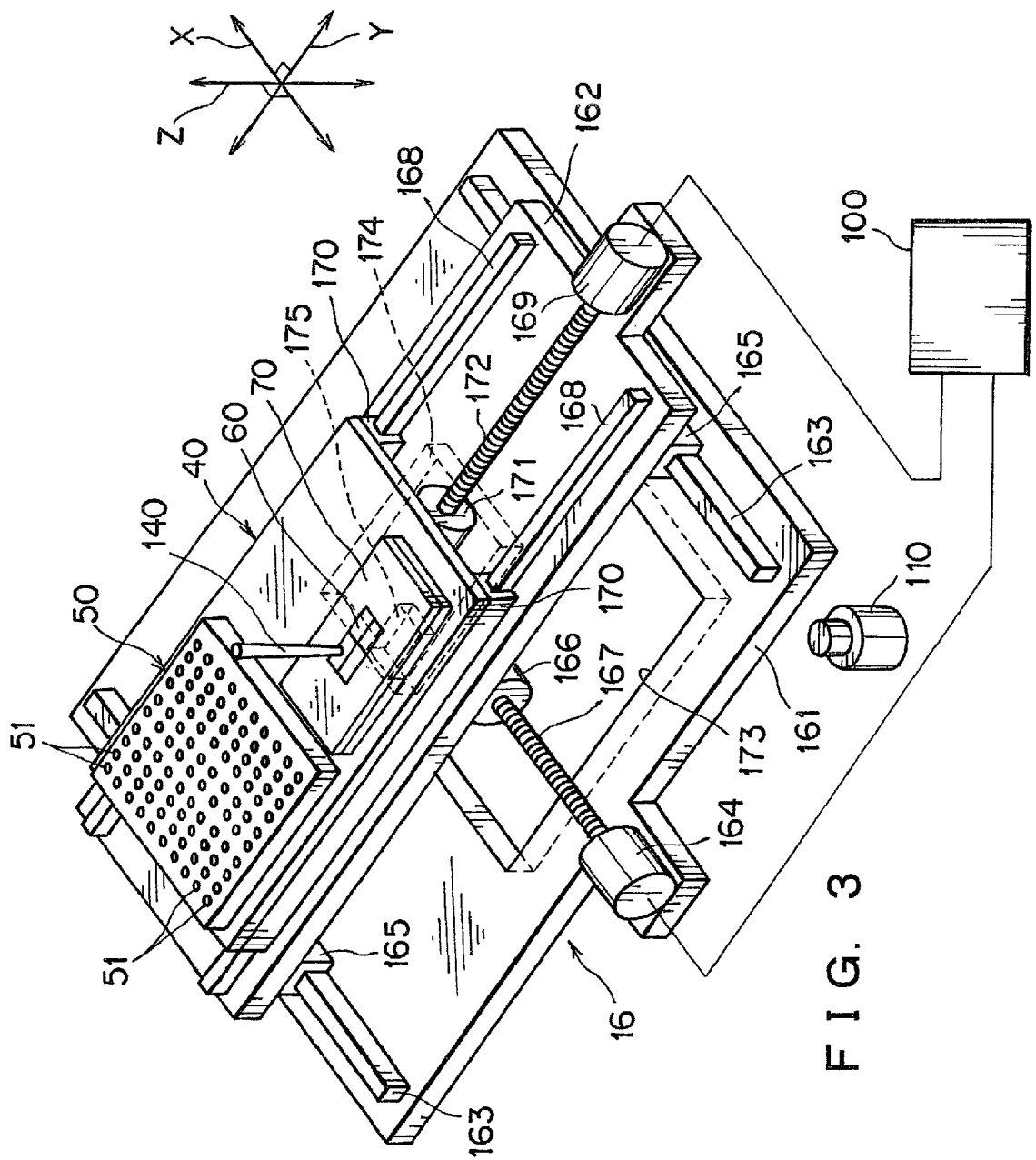
FIG. 3 is a perspective view showing details of a moving section and a mounting table shown in FIG. 2.

FIG. 3 is a perspective view showing details of the moving section 16 and the mounting table 40 shown in FIG. 2.

As shown in FIG. 3, the moving section 16 includes a table 161 and a table 162 disposed on said table. The table 161 is secured to the supporting table 30, and the table 162 mounted thereon can be positioned by being moved along the X-direction. On the table 162, the mounting table 40 is mounted so as to be capable of being positioned by being moved along the Y-direction.

Guide rails 163 and 163 and a motor 164 are provided on an upper face of the table 161. Engaging members 165 and 165 each having a U-shaped cross section and a nut 166 are provided on a lower face of the table 162. The engaging members 165 and 165 movably engaged with the guide rails 163 and 163, respectively. A feed screw 167 of the motor 164 is screwed to the nut 166.

The motor 164 is electrically connected to a control unit 100. By operating the motor 164 in response to a command from the control unit 100 to rotate the feed screw 167, the table 162 is positioned by being moved along the X-direction.

Guide rails 168 and 168 and the motor 169 are provided on an upper face of the table 162. Engaging members 170 and 170 each having a U-shaped cross section and a nut 171 are provided on a lower face of the mounting table 40. The engaging members 170 and 170 movably engage with the guide rail 168 and 168, respectively. A feed screw 172 of the motor 169 is screwed to the nut 171.

The motor 164 is electrically connected to the control unit 100. By operating the motor 164 in response to a command from the control unit 100 to rotate the feed screw 172, the mounting table 40 is positioned by being moved along the Y-direction.

The tables 161 and 162 have openings 174 and 173, respectively, and further, the mounting table 40 includes an opening 175. These openings 173, 174 and 175 have respective sizes that they always overlap with each other even if the table 162 moves in the X-direction and the mounting table 40 moves in the Y-direction. Through these openings 173, 174 and 175, light L from an objective lens 110 side of the measuring section 14 is illuminated on the microparticles on the measurement chip 60 on the mounting table 40.

Also, even if the table 162 has moved in the X-direction and the mounting table 40 has moved in the Y-direction, light L from the objective lens 110 side passes through the opening 173, 174 and 175 and is illuminated on microparticles on the measurement chip 60 on the mounting table 40. That is, fluorescence can be produced from microparticles at any relative position between the tables 161, 162 and the mounting table 40.

Figure 4:
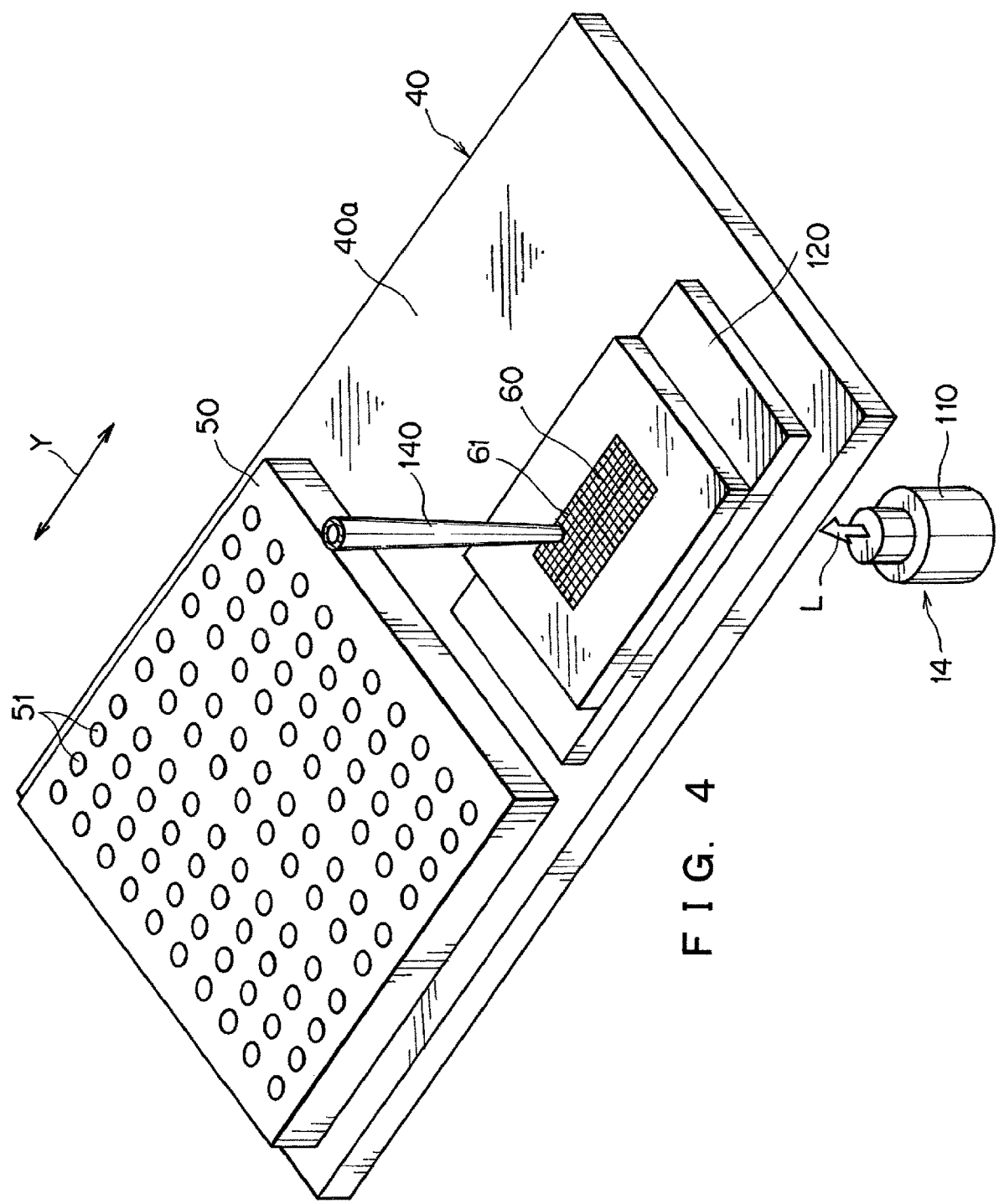
FIG. 4 is a perspective view showing a configuration of a receiving plate and a measurement chip on the mounting table shown in FIG. 3.

FIG. 4 is a perspective view showing a configuration of the receiving plate 50 and a measurement chip 60 on the mounting table 40 shown in FIG. 3.

The mounting table 40 is, for example, a rectangular plate-like member. The receiving plate 50 and the measurement chip 60 are detachably mounted on a mounting face 40a of the mounting table 40 and are arranged along the Y-direction.

The receiving plate 50 is a plate-like member. The receiving plate 50 includes a large number of wells 51 arranged in a matrix at a constant interval along the X-direction and the Y-direction. The wells 51 are collecting-and-storing sections each capable of, when microparticles such as organism cells are discharged sequentially from a suction-ejection capillary 140, separately collecting and storing microparticles which have been discharged sequentially. For example, the well 51 of the receiving plate 50 is a recessed portion having, for example, a substantially U-shaped vertical direction cross section or a recessed portion having a cup-shape.

The measurement chip 60 is secured to a mounting surface 40a of the mounting table 40 by a securing member 120, and the fixing member 120 is positioned and secured at a predetermined position on the mounting table 40.

Figure 5:
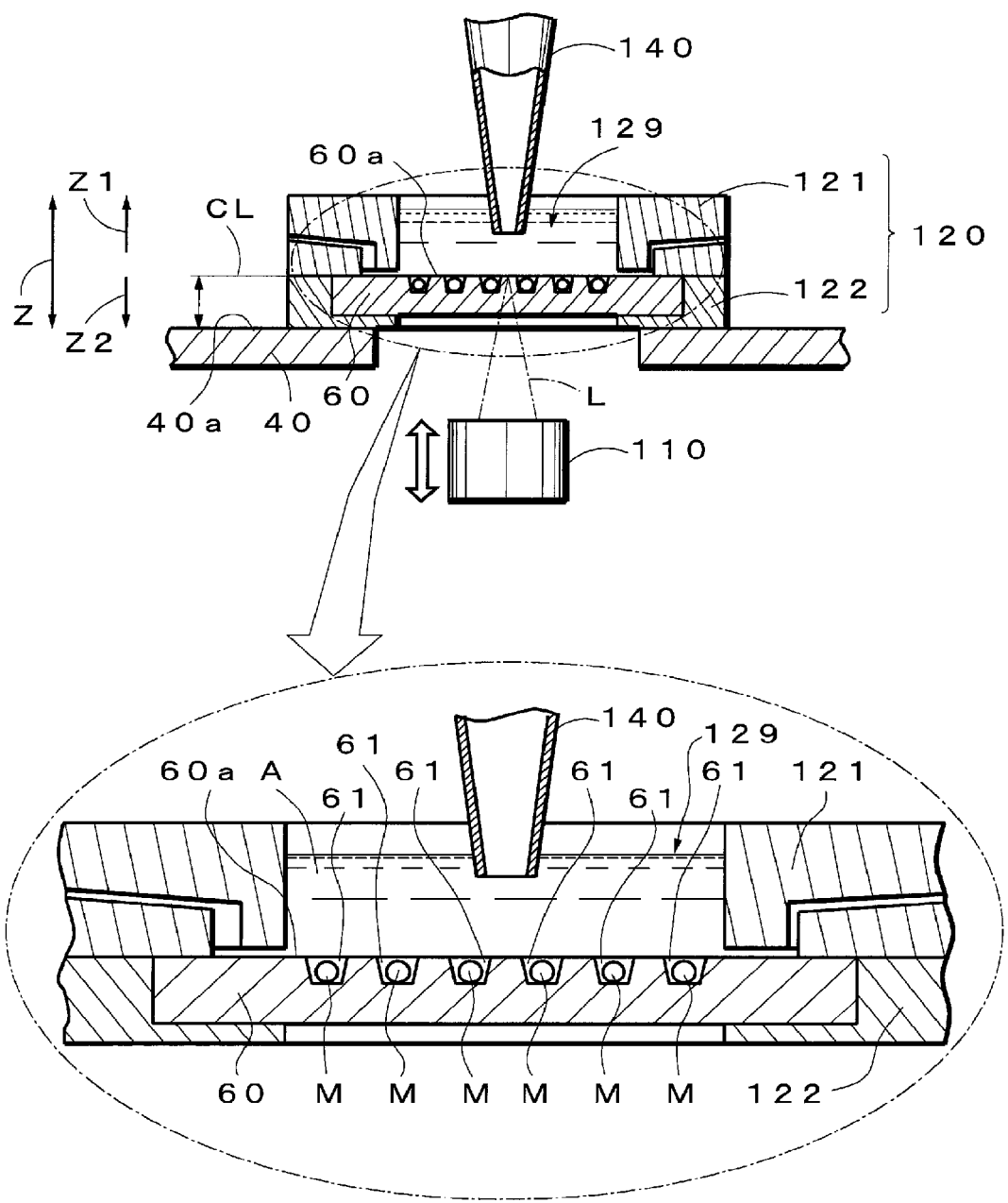
FIG. 5 is an enlarged sectional view showing a configuration of the measurement chip and a measurement chip securing member.

FIG. 5 is an enlarged sectional view showing a configuration of the measurement chip 60 and the securing member 120 of the measurement chip. The securing member 120 secures and holds the measurement chip 60 at a position on a reference plane CL which is at a certain level with respect to the mounting surface 40a of the mounting table 40. Specifically, the securing member 120 includes securing members 121 and 122 that cooperate to hold the measurement chip 60. The securing member 121 and 122 are substantially frame-shaped structures disposed to surround an edge portion of the measurement chip 60.

The measurement chip 60 is disposed between the securing members 121 and 122 and in pressure contact with each of the securing members 121 and 122 by being sandwiched with the securing members 121 and 122. Thus, sealing property between the measurement chip 60 and the securing member 121 is ensured.

With the measurement chip 60 and the securing member 121 being in pressure contact, the upper face 60a of the measurement chip 60 is positioned at a reference level CL via the securing member 122. Thereby, a distance in the Z-direction between the upper face 60a of the measurement chip 60 from an objective lens 110 of the measuring section 14 and the receiving plate 50 can be controlled accurately. In other words, a position of a microparticle M in the well 61 of the measurement chip 60 and the distance between the objective lens 110 of measuring section 14 and the receiving plate 50 can be managed accurately.

Further, the securing member 121 includes a liquid holding section 129 that retains a liquid A and provided at a central part in a direction of its plane and above the measurement chip 60, and that is capable of retaining various liquids such as a culture medium, a reagent solution, and a reaction liquid. In other words, the liquid holding section 129 is formed in an internal space of the securing member 121 that is a substantially frame-shaped structure. The securing member 121 can be opened and closed with respect to the securing member 122 using, for example, a hinge mechanism section, not shown. Thereby, the measurement chip 60 in the securing member 120 can be removed and replaced with a new measurement chip 60. Details of the securing member 120 will be described below.

The measurement chip 60 is made of a translucent material, e.g., glass and plastics, and, a large number of wells 61 are arranged in a matrix in the upper face 60a thereof. For example, each of the wells 61 is a recessed portion having a substantially a trapezoid or a substantially cup-shaped vertical cross section, and a horizontal cross section of the well 61 is preferably substantially circular. Each well has such a size that a single microparticle M can be stored therein by dispensing or batch-introducing the microparticles M.

Further, the collecting section 13 is provided with a suction-ejection capillary 140 that sorts the identified microparticle M as a target sample (FIG. 1). The suction-ejection capillary 142 is a hollow member having a tapered shaped with its diameter decreasing along the Z2 direction (downward direction) and has a conduit formed therethrough.

By illuminating light L onto a region of the measurement chip 60 in which a plurality of wells 61 are provided, the measuring section 14 causes fluorescence to be produced from microparticles M in the region and receives the fluorescence (FIG. 1). The fluorescence received from the microparticles M is subjected to an image analysis by an image analyzing section 15.

Specifically, by illuminating the measurement chip 60 and microparticles M retained in the measurement chip 60 with light guided from at least one light source, the measuring section 14 acquires shape and position information obtained from transmitted light, reflected light or fluorescence, and luminance information such as luminescence and chemiluminescence with a resolution finer than an average size of the microparticles, and also acquires information such as a shape of the measurement chip itself or a positional coordinate or a size of the well 61 disposed in the measurement chip 60.

Further, the measuring section 14 has an objective lens 110, and the objective lens 110 guides light to the measurement chip 60. The objective lens 110 is disposed below the measurement chip 60 and the moving section 16, and the suction-ejection capillary 140 is disposed above the measurement chip 60 and the moving section 16. Accordingly, the measurement chip 60 and the moving section 16 thereof can be disposed between the objective lens 110 and the suction-ejection capillary 140.

Further, the measuring section 14 includes the pump light source 181 as a light source and the fluorescence filter unit 183 comprising an optical filter (pump filter) 184 for selecting only a desired pump wavelength band among light illuminated from the pump light source 181, an optical filter (fluorescence filter) 185 for selecting only a desired wavelength band of the optical information from the measurement chip 60, and a dichroic mirror 186 for changing an optical path length in accordance with a difference between wavelength bands of the pump light and the optical information. Further, the measuring section 14 has the objective lens 110 for guiding light emitted from the pump light source 181 to the measurement chip 60 and for collecting optical information obtained from the measurement chip 60, a focus unit 187 having an automatic focus function capable of moving the objective lens 110 in an optical axis direction, and a light receiving section 188 for detecting optical information from a measurement target. The fluorescence filter unit 183 and the light receiving part 188 are fixed to an epifluorescence unit 190.

As to the measuring section 14, a pump light source 181 includes, for example, a laser source and a mercury lamp. A shutter unit 182 is disposed between the pump light source 181 and a fluorescence filter unit 183. The shutter unit 182 is capable of blocking light L produced by the pump light source 181 directly in front of the fluorescence filter unit 183 in a case where the light L is not illuminated on the microparticles M on the measurement chip 60.

Further, the measuring section 14 includes a half mirror, not shown. By switching between the half mirror and the fluorescence filter unit 183, a part of the light from the pump light source 181 is irradiated on an observation target, and at the same time, a part of the reflected light from the observation target is guided to a light receive part 188. Thereby, shape and position information of the upper face 60a of measurement chip 60 and the well 61 formed on the upper face can be measured.

In this measuring section 14, by rotating a plurality of objective lens 110a, 110b . . . , for example, in a revolver manner, an objective lens of a required magnification can be positioned at a position below the measurement chip 60. By operating the motor 189 in accordance with, for example, a command from the control unit 100, the objective lens 110, for example, located at a position below the measurement chip 60 is moved and positioned along the Z-direction, the focus unit 187 can perform focus adjustment of the objective lens 110 on microparticles M in the measurement chip 60.

The image analyzing section 15 calculates a fluorescence luminance of a microparticle M1 emitting fluorescence of at least a maximum intensity from among a plurality of microparticles M in each well 61.

Specifically, by analyzing the measured shape information and optical information, the image analyzing section 15 acquires data for confirming that a microparticle M1 satisfying a luminance condition which can be set by the observer exists at least in each well 61. The image analyzing section 15 extracts optical information from the microparticles by matching and verifying the positional coordinate information of the well 61 from the transmitted light or the reflected light, and the optical information of fluorescence and chemiluminescence. Further, the measuring section 14 has an autofocus function. The measuring section 14 is capable of performing measurement while being focused at a predetermined position and determining a positional relationship between the distal end portion of the suction-ejection capillary 140 and an upper face of the measurement chip 60 by performing an autofocus on both of them.

The control unit 100 detects, in a plane constituted by an X-direction and a Y-direction, a position of the well 61 in which the microparticle M1 emitting fluorescence of a maximum luminance satisfying the collecting conditions is contained. Then, by supplying a control driving signal to the motors 164 and 169 of FIG. 3, the control unit 100 can position the well 61 of the measurement chip 60 on the moving section 16 directly beneath the suction-ejection capillary 140. That is, the suction-ejection capillary 140 is configured to be capable of targeting a particular well and sucking a microparticle in the well. Further, the suction-ejection capillary 140 can suck, from a selected well among a plurality of wells, in other words, from a well containing a microparticle satisfying predetermined collecting conditions, at least one microparticle. Further, the suction-ejection capillary 140 can eject the selected at least one microparticle into a predetermined well 51 in the receiving plate 50.

For example, with the screening apparatus 1 that is configured as described above, a target sample is collected in a manner described below.

Figure 7:
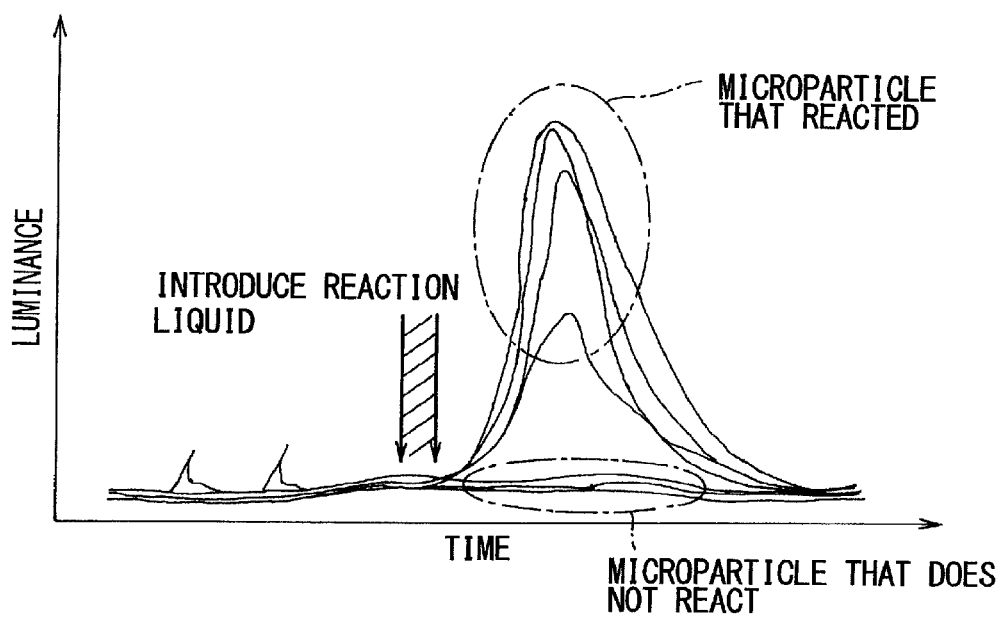
FIG. 7 is a diagram for explaining time lapse measurement of a sample using a configuration of the related art.

As shown in FIG. 6, firstly, location information of the measurement chip 60 is acquired from information regarding a reference position of the measurement chip and correction parameters or the like (step S1). Thereafter, an image analysis is performed to acquire center position coordinate information of each well (step S2). Then, a light is illuminated to acquire optical information of a microparticle (sample) and a luminance analysis is carried out (step S3). The luminance analysis may be performed by, for example, as shown in FIG. 7 described later, introducing a reaction liquid into each of the wells to cause the microparticles in the well to produce fluorescence, and measuring a temporal variation of this fluorescence information. Also, information of microparticles that is already emitting light may be measured regardless of introduction of a reaction liquid. Also, the number of microparticles stored in each well on the measurement chip 60 may be counted.

Then, based on the acquired fluorescence information, collecting conditions may be set as collecting conditions of a microparticle required by a user, for example, conditions in which a luminance of a certain fluorescence has exceeded a predetermined threshold, or a condition in which, when a plurality of fluorescence (e.g., colors of the fluorescence are different) are used, a luminance of at least one of the fluorescence has exceeded a predetermined threshold, or any combination thereof. Alternatively, for a luminance of any fluorescence, conditions to be excluded from collecting (the one which is lower than a threshold) may be combined. Some conditions determined in a manner described above are input (step S4), and a microparticle that satisfies the aforementioned collecting conditions is identified as a target sample (step S5). Then, a center position of the capillary is acquired by an image analysis, and either the center position or a position shifted towards the center position by a predetermined distance is set as a center position of the well during the collecting of the microparticle (position information) (step S6). The center position of each of the wells in which a target sample is contained is moved to match the center position of the well during the collecting of the microparticle, which is set in step S6, and target samples identified in step S5 are collected sequentially (step S7). The collected sample is placed in a predetermined well in the receiving plate 50 which was set in advance by the user.

In order to identify a sample with a high accuracy using the method shown in FIG. 6, it is necessary to accurately acquire time lapse images of fluorescence emitted by microparticles M such as cells. For example, after having received microparticles on the measurement chip 60, when a reagent solution is introduced into a liquid retaining section 129 to replace the culture medium with the reagent solution, microparticles M, which are to be target samples, are stimulated and emit fluorescence after an elapse of a predetermined time (FIG. 7). The time elapsed since the beginning of replacement of the culture medium with the reagent until each cell has reacted is normally constant for the same target sample, but a reaction time may vary and also a fluorescent intensity may vary depending on factors such as positions of the wells in which respective cells are stored. Therefore, at the measuring section 14, it is required to measure the degree of fluorescence of each microparticle after introduction of the reagent solution with a high sensitivity and in a timely manner.

Here, in order to clearly distinguish non-target samples from target samples, it is desirable to increase fluorescence intensity of cells that are target samples by causing an appropriate reaction of the cells immersed in the culture medium in the well with the reagent solution to be subsequently introduced. According to the present disclosure, a high precision identification of the target samples is enabled by controlling the liquid surface in the liquid retaining section 129 formed on the measurement chip 60.

Figure 8:
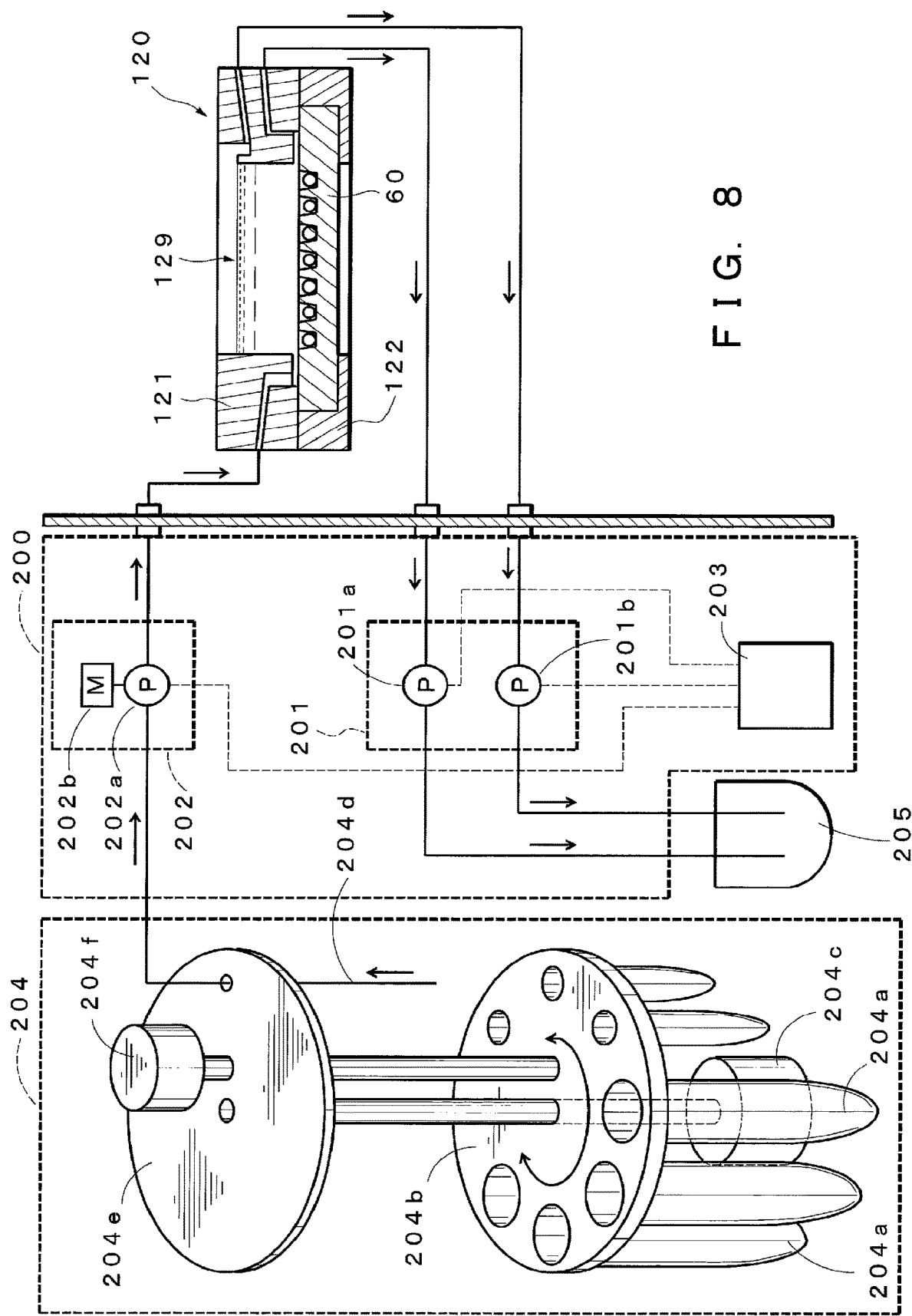
FIG. 8 is a diagram showing a configuration of a liquid level controlling section of the present disclosure.

The screening apparatus 1 of the present disclosure is provided with a liquid level controlling section 200 as shown in FIG. 8. The liquid level controlling section 200 is capable of separately controlling an amount and a draining timing of a liquid drained from the liquid retaining section 129 and an amount and an introducing timing of a liquid introduced into the liquid retaining section 129. Specifically, the liquid level controlling section 200 has a liquid delivering section 201 (first liquid delivering section) disposed downstream of a draining section (to be described below) of the securing member 120, a liquid delivering section 202 (second liquid delivering section) disposed upstream of an introducing section (to be described later) of the securing member 120, and a control unit 203 that is configured to control an operation of the liquid delivering sections 201 and 202. Provided upstream of the liquid delivering section 202 is a liquid switchover section 204 for switching between and supplying various liquids such as a culture medium and a reagent solution to the liquid delivering section 202. The liquid level controlling section 200 is provided separate from the aforementioned control unit 100, but it is also possible to use a common control unit.

The liquid delivering section 201 comprises pumps 201a and 201b connected to two draining sections of the securing member 120 via tubes, respectively, and, is capable of changing flow rates by voltage variation based on a signal from the control unit 203. Provided downstream of the pumps 201a and 201b is a waste liquid tank 205 that stores liquid drained through the respective pumps.

The liquid delivering section 202 includes a pump 202a connected to an introducing section described below through a tube and a stepping motor 202b attached to the pump, and is capable of sending out a little liquid with a high accuracy.

The control unit 203 is electrically connected to the pumps 201a, 201b and the pump 202a (or a stepping motor 202b), and individually controls operation of each of the pumps in response to a signal from outside or ON/OFF of a timer.

The liquid switchover section 204 is a revolver-type switchover mechanism, and includes a rotating platform 204b that holds test tubes 204a in which several kinds of liquid such as a culture medium or a reagent solution are contained, a stepping motor 204c that rotates the rotating platform, a holder 204e that is attached above the rotating platform 204b and secures a tube 204d connected to the liquid delivering section 202, and an alternate current motor 204f that causes a relative movement between the rotating platform 204b and the holder 204e in a vertical direction (longitudinal direction) to insert an end portion of the tube 204d into a predetermined test tube. The stepping motor 204c and the alternate current motor 204f are electrically connected to the control unit 203 or another control unit, not shown, respectively, and rotate and move the rotating platform 204b and the holder 204e in response to a signal from the control unit 203. Thus, a desired liquid can be sent out to the liquid delivering section 202.

Figure 9A:
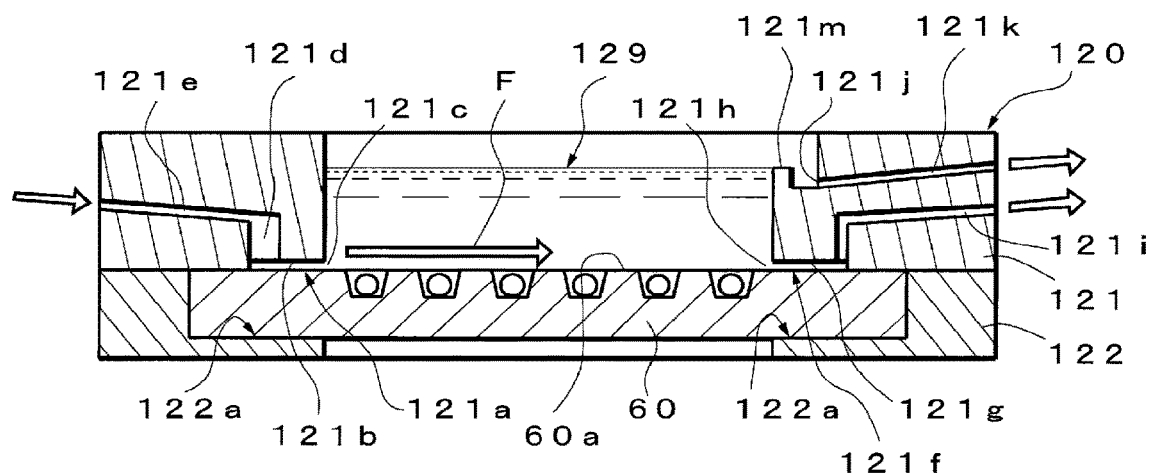
FIG. 9A is a cross sectional view showing details of the securing member of FIG. 5.
Figure 9B:
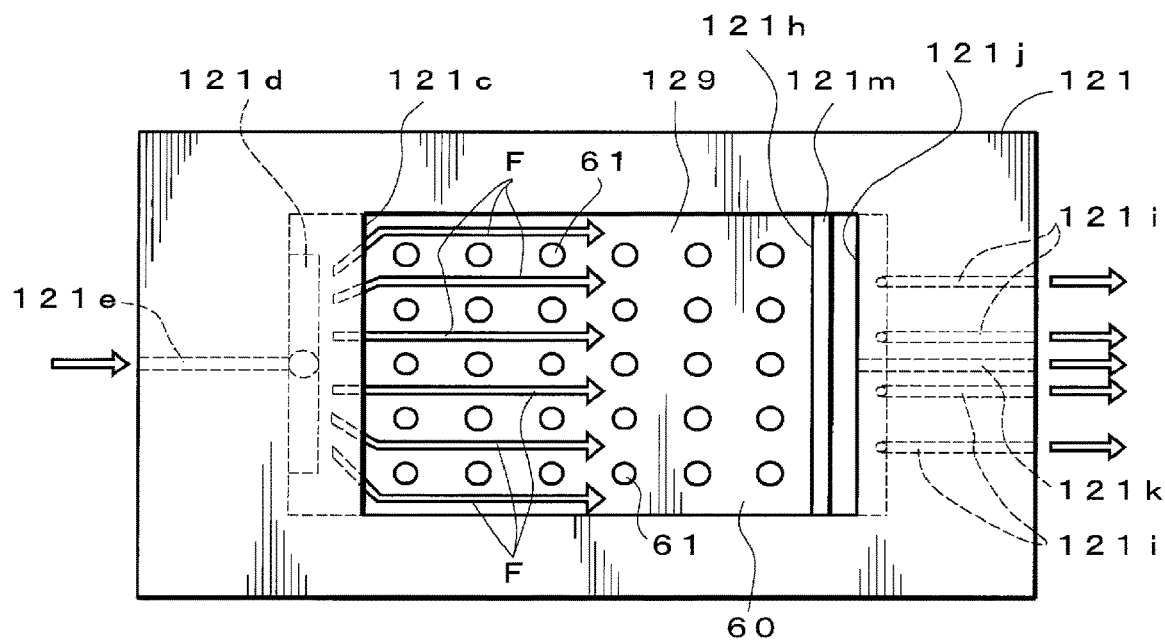
FIG. 9B is a plan view showing details of the securing member of FIG. 5.

FIGS. 9A and 9B are a cross sectional view and a plan view, respectively, showing details of the securing member 120 connected downstream of the liquid delivering section 202.

The securing member 120 includes securing members 121 and 122 that sandwich an outer periphery of the measurement chip 60 in a vertical direction to secure the measurement chip 60 inside the securing member. Specifically, the securing member 122 that is disposed at a lower position has a substantially frame-shaped structure and has a stepped portion 122a at an inner part of an upper face thereof. The outer periphery of the measurement chip 60 is fitted in the stepped portion. Thereby, a side face and a lower face of the measurement chip 60 are supported by the securing member 122. The stepped portion in which the outer periphery of the measurement chip 60 is fitted may be provided in the securing member 121 that is disposed at an upper position.

The securing member 121 disposed at an upper position has a substantially frame-shaped structure, and an inner part of a lower face thereof is in contact with an upper face of the measurement chip 60. Thereby, the upper face 60a of the measurement chip 60 is supported by the securing member 121.

The securing member 121 has a stepped portion for introducing liquid 121a at an inner part of the lower face thereof. The stepped portion for introducing liquid 121a has such a step height that a slight clearance is created between a lower face 121b of the stepped portion for introducing liquid 121a and an upper face 60a of the measurement chip 60 when the securing member 121 is placed on the measurement chip 60. A substantially flattened opening at an end part of the space formed by the clearance constitutes an introduction port described below.

Further, the securing member 121 has an introduction port 121c having a flattened shape, a buffer 121d provided above the introduction port, and a flow channel 121e (a first flow channel). The introduction port 121c is formed between a lower face 121b of the stepped portion 121a and an upper face 60a of the measurement chip 60 and provided to extend in a direction of a plane of the measurement chip 60. The buffer 121d is configured to supply a liquid to the introduction port 121c. The flow channel 121e is connected to the buffer and supplies a liquid from the liquid delivering section 202 to the buffer 121d. The introduction port 121c, the buffer 121d and the flow channel 121e constitute the introducing section of the present disclosure.

The liquid supplied from the liquid delivering section 202 flows through the flow channel 121e and is temporarily retained in the buffer 121d. The liquid retained in the buffer 121d is sent out to the liquid retaining section 129 with a predetermined pressure through the introduction port 121c that is formed with a slight clearance. By the introduction port 121c, the liquid is supplied directly above the measurement chip 60 and along the upper face 60a of the measurement chip (liquid flows F). Also, according to the present embodiment, the introduction port 121c is formed to extend over an entirety of the liquid retaining section 129 in a widthwise direction in a plan view (FIG. 9B). Thereby, liquid sent out through the introduction port 121c is supplied over the entirety of the liquid retaining section 129 in a widthwise direction with almost the same timing. Therefore, liquid flows F of substantially the same speed in the widthwise direction of the measurement chip can be produced on the measurement chip 60.

Further, the buffer 121d is provided to extend in a direction of a plane of the measurement chip 60 and also to extend in a direction substantially parallel to the introduction port 121c (FIG. 9B). Therefore, the liquid retained in the buffer 121d is positively supplied over an entirety of the introduction port 121c in a lateral direction, and thus the liquid can be positively supplied over an entirety of the liquid retaining section 129 in a widthwise direction through the introduction port 121c. The securing member 121 need not be provided with a buffer 121d, and may be configured in such a manner that liquid is directly supplied to the introduction port 121c through the flow channel 121e.

Also, the securing member 121 has a stepped portion for draining liquid 121f at an inner part of the lower face thereof. The stepped portion for draining liquid 121f has such a step height that a predetermined clearance is created between a lower face 121g of the stepped portion for draining liquid 121f and the upper face 60a of the measurement chip 60 when the securing member 121 is placed on the measurement chip 60, and it is usually greater than the step height of the stepped portion for introducing liquid 121a.

Further, the securing member 121 has a draining port 121h (first draining port) formed between the lower face 121g of the stepped portion for draining liquid 121f and the upper face 60a of the measurement chip 60, and a plurality of flow channels 121i (second flow channel) through which the liquid is sent out from the draining port to the liquid delivering section 201.

The liquid in the liquid retaining section 129 is sent out through the draining port 121h at a predetermined pressure. Here, by the draining port 121h, liquid is drained directly above the measurement chip 60 and along the upper face 60a of the measurement chip. Further, in the present embodiment, in a plan view, the draining port 121h is formed over an entirety of the widthwise direction of the liquid retaining section 129, and the plurality of flow channels 121i are juxtaposed along the width direction of the liquid retaining section 129. Therefore, the liquid in the liquid retaining section 129 can be sent out at an approximately uniform speed over an entirety of the widthwise direction.

Also, the securing member 121 has a draining port 121j (second draining port) formed above the draining port 121h and a flow channel 121k (third flow channel) that drains the liquid through the draining port to the liquid delivering section 201. The draining port 121h, the flow channel 121i, the draining port 121j and the flow channel 121k constitute the draining section of the present disclosure. The draining port 121j and the flow channel 121k do not necessarily have to be provided, and in such a case, the draining port 121 and the flow channel 121i constitute the draining section of the present disclosure.

Further, the securing member 121 has a dam portion 121m provided in the vicinity of the draining port 121j. In the present embodiment, in a plan view, the dam portion 121m is formed over an entirety of the liquid retaining section 129 in the widthwise direction (FIG. 9B). Therefore, the highest liquid level can be positively maintained without overflowing the liquid in the liquid retaining section 129.

Figure 10A:
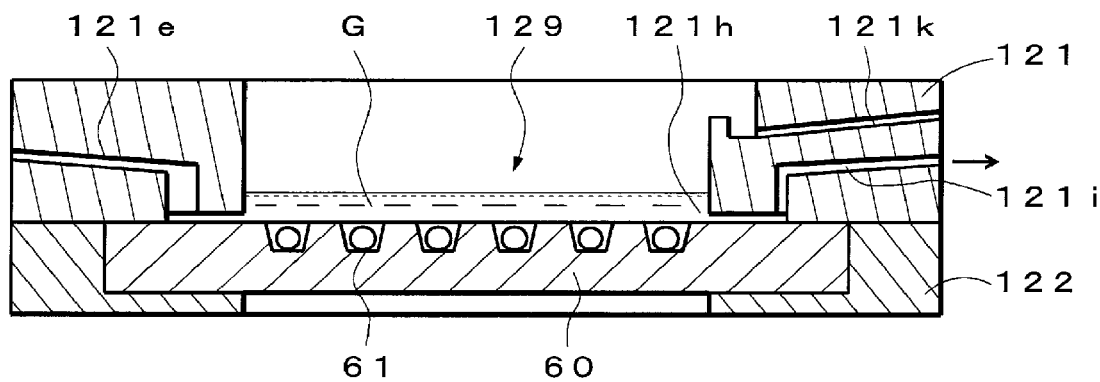
FIG. 10A is a diagram for explaining how a liquid is drained from a liquid retaining section formed on a measurement chip of the present disclosure.
Figure 10B:
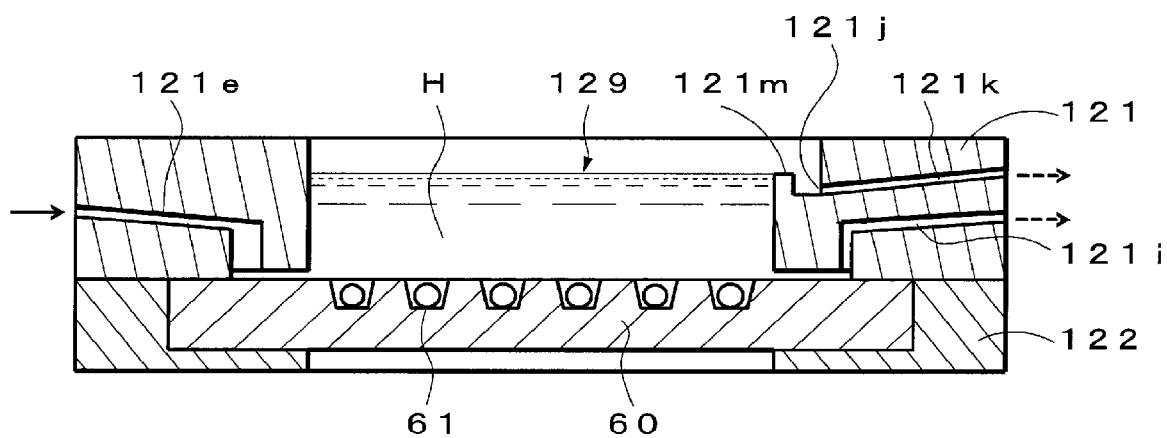
FIG. 10B is a diagram for explaining how a liquid is introduced into a liquid retaining section formed on a measurement chip of the present disclosure.
Figure 10C:
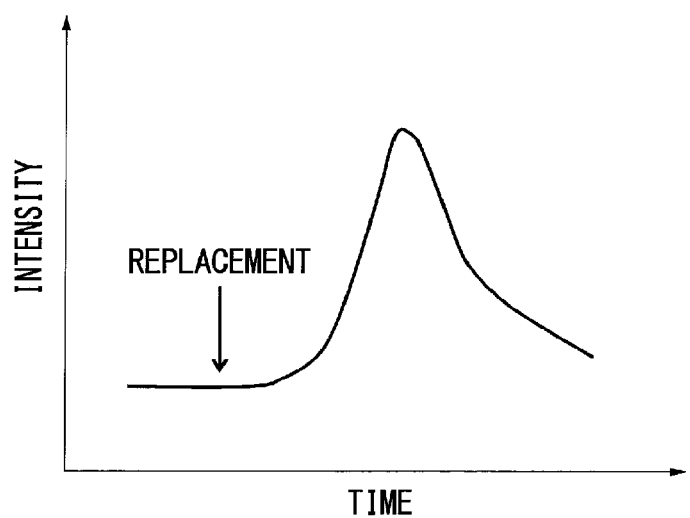
FIG. 10C is a graph showing a magnitude of detected light intensity of the present disclosure.

FIG. 10A is a diagram for explaining how a liquid is drained from the liquid retaining section 129 formed on the measurement chip 60. FIG. 10B is a diagram for explaining how the liquid is introduced into a liquid retaining section 129 formed on a measurement chip 60. FIG. 10C is a graph showing a magnitude of light intensity of a detected microparticle. Referring to FIGS. 10A to 10C, an exemplary case in which a reference liquid such as a culture medium and a liquid for searching such as a reagent solution are replaced will be described.

Figure 11A:
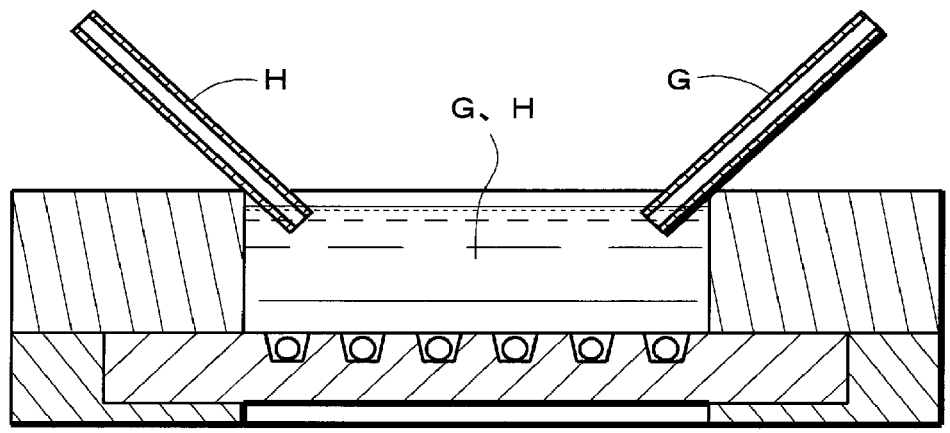
FIG. 11A is a diagram for explaining how a liquid is drained from a measurement chip of the related art.

As the culture medium is sent out from the liquid delivering section 202, the culture medium is introduced into the liquid retaining section 129 through the introduction port 121c, and the culture medium of a predetermined quantity is retained in the liquid retaining section 129. Then, it is drained from the liquid retaining section 129 through the draining port 121h before introducing the reagent solution. After the draining of the culture medium, a small amount of culture medium C remains in the liquid retaining section 129, and the liquid level is directly above the well 61 (FIG. 10A). With the small amount of culture medium G' remaining, the reagent solution to be introduced thereafter will flow directly above the measurement chip 60 with a speed of the liquid flow F faster than a case which a large amount of culture medium is remaining in the liquid retaining section 129. Thus, it is possible to make the reagent solution reach faster to almost all the wells 61 in the measurement chip 60. On the other hand, when a reagent solution H is introduced from above while draining the culture medium G as shown in FIG. 11A, a large amount of culture medium is remaining in the liquid retaining section 129, and thus the speed of the liquid flow directly above the measuring chip 60 becomes slower due to drag, and a rate of reaction of the cell that is a target sample becomes slow.

Figure 11B:
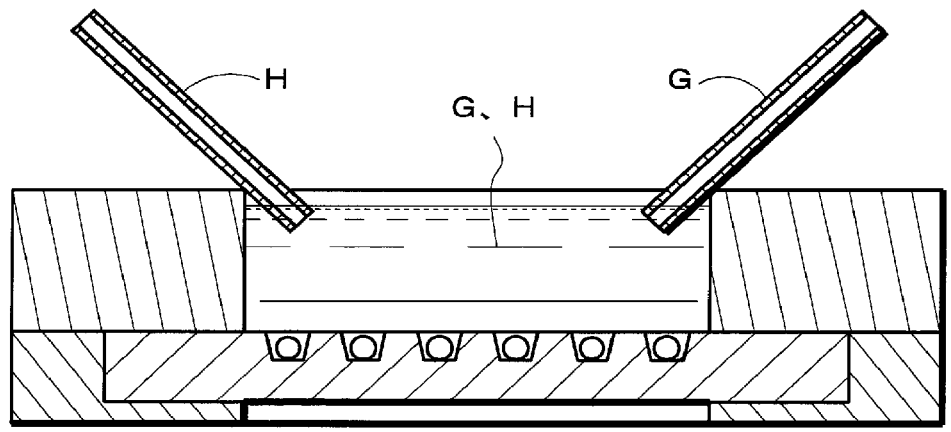
FIG. 11B is a diagram for explaining how a liquid is introduced on a measurement chip of the related art.
Figure 11C:
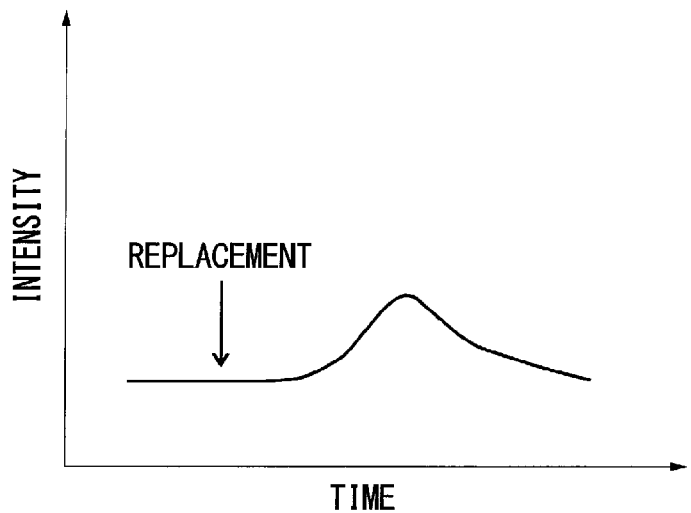
FIG. 11C is a graph showing a magnitude of light intensity of the related art.

Thereafter, a reagent solution H is introduced into the liquid retaining section 129 through the introduction port 121c (FIG. 10B). Here, because the amount of culture medium G' remaining in the liquid retaining section 129 is minimum, the reagent solution H introduced therein is almost not diluted. Thus, concentration of the reagent solution H introduced into the liquid retaining section 129 can be maintained at a concentration that is substantially the same as that of the reagent solution H sent out from the liquid delivering section 202, and it becomes possible to cause reaction at a desired concentration. Accordingly, a light emission intensity of a cell that is target sample can be made stronger (FIG. 10C) and it becomes possible to improve sorting accuracy. On the other hand, when the reagent solution H is introduced from above while draining a culture medium G as shown in FIG. 11B, the reagent solution H is diluted with a large amount of culture medium, and a light emission intensity of a cell that is a target sample becomes weaker (FIG. 11C).

With the present disclosure, a culture medium is drained before introducing the reagent solution, and a culture medium of a minimum quantity required to achieve the aforementioned object is remained. Then, with a small amount of culture medium G remaining in the liquid retaining section 129, the reagent solution H is supplied directly above the measurement chip 60.

Figure 12:
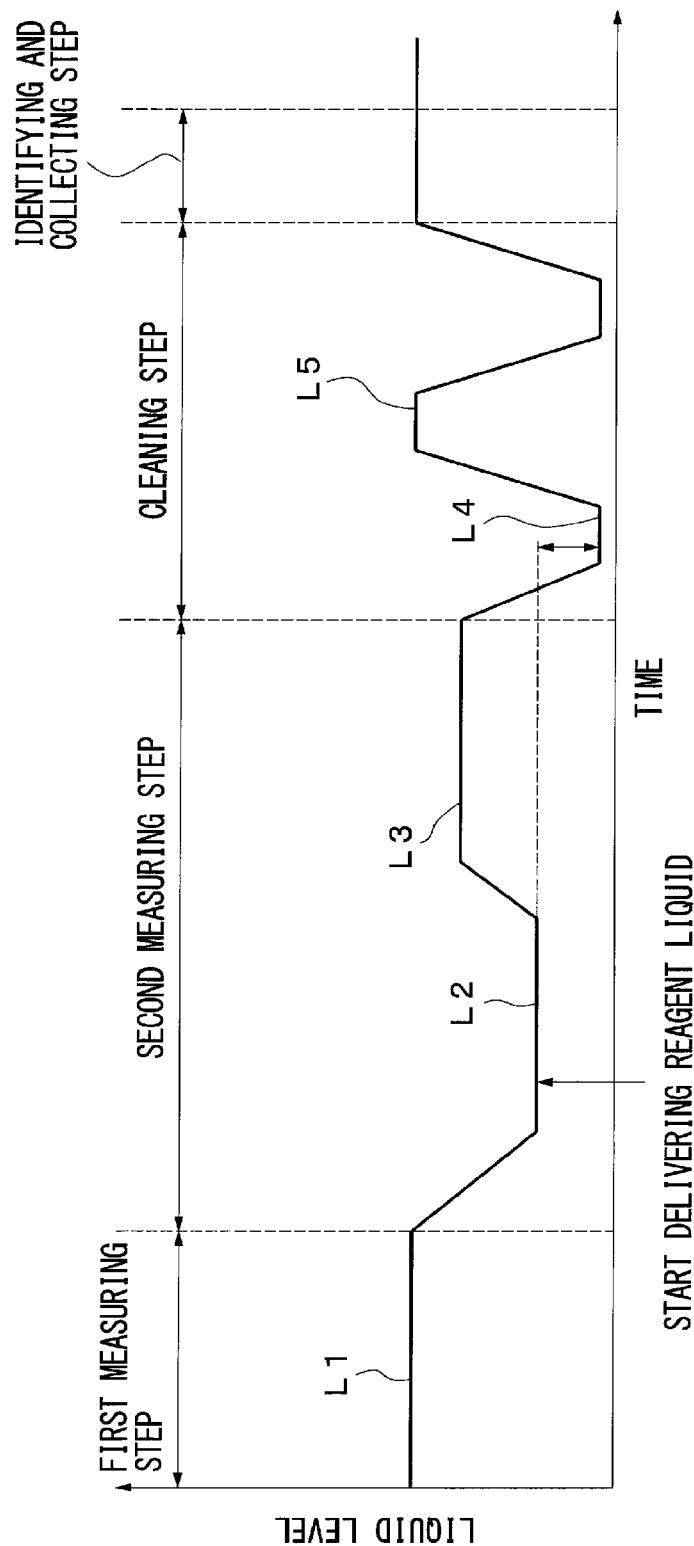
FIG. 12 is a diagram showing a temporal change of a liquid level in the liquid retaining section as a result of liquid level control carried out by the liquid level controlling section shown in FIG. 8.

FIG. 12 is a diagram showing a temporal change of the liquid level of the liquid retaining section 129 in a case where liquid level control is carried out by the liquid level controlling section 200 shown in FIG. 8. Hereinafter, a liquid level control step that is carried out in a screening method of the present disclosure will be described.

At a liquid level controlling section 200, first, a culture medium (reference liquid) is introduced on the measurement chip 60, and then position coordinate information of the well 61 in the measurement chip and optical information emitted by a cell (microparticle) in the well 61 are measured, and thereafter, the culture medium is drained (first measurement step). When measuring the position coordinate information of the well 61, the liquid level in the liquid retaining section 129 is maintained at a predetermined liquid level L1 (first liquid level), and, after the measurement has terminated, a culture medium is drained and the liquid level is L2 (L1>L2).

Thereafter, the reagent solution (liquid for searching) is introduced on the measurement chip 60 and optical information emitted by the cell (microparticle) in the well 61 is measured (second measurement step). When measuring the optical information emitted from the cell, the liquid level is maintained at approximately liquid level L2 (second liquid level). In this measurement step, when an amount of reagent solution introduced into the liquid retaining section 129 is small, reaction of the cells may vary due to surface tension. Therefore, in order to prevent this, the liquid level may be gradually or progressively increased to liquid level L3 (L2<L3) (third liquid level).

Thereafter, the reagent solution in the measurement chip 60 is drained, the culture medium is introduced and drained, and the measurement chip 60 is cleaned (cleaning step). When draining the reagent solution in the measurement chip 60, the liquid level adjusted to liquid level L4 (L3>L4) (fourth liquid level) and thereafter, a culture medium is introduced and the liquid level is adjusted to liquid level L5 (L4<L5). In the cleaning step, by adjusting the liquid level at L4, the reagent solution is removed as much as possible from the measurement chip 60, and thereafter, a large amount of culture medium is introduced to adjust the liquid level at L5, and a cleaning effect by a culture medium can be obtained effectively. The cleaning step by introducing and draining the culture medium may be performed twice as shown in FIG. 12, or may be performed once or more than three times. With this cleaning step, the cells (microparticles) that have reacted in the reagent solution (liquid for searching) are sufficiently replaced with the culture medium, and thus reaction can be made moderate, and it becomes possible to acquire optical information accurately in a subsequent measurement using another reagent solution. Also, an identification step and a collection step described below may be performed after having repeated several cycles each including the first measurement step, the second measurement step and the cleaning step.

Thereafter, based on the position coordinate information and the optical information thus measured, microparticles which have satisfied the predetermined collecting condition are identified as target samples (identification step) and the target samples are collected (collection step). Here, the liquid level of the liquid surface receiving portion 129 is maintained, for example, at liquid level L5.

As set forth above, according to the present embodiment, since the liquid level controlling section 200 controls the liquid level in the liquid retaining section 129 formed on the measurement chip 60, the liquids in the well 61 that stores a cell and the liquid retaining section 129 can be replaced accurately and effectively during each step of sorting. Therefore, optical information of the cell in the well 61 can be acquired accurately and sorting accuracy can be improved.

Also, since the amount and the draining timing of the liquid drained from the liquid retaining section 129 and the amount and the introducing timing of a liquid introduced into the liquid retaining section can be controlled separately, the liquid level of liquid retaining section 129 can be changed to a desired height and optical information of the cell in the well 61 can be acquired more accurately.

Particularly, by keeping the liquid surface of the culture medium on the measurement chip 60 at a stable position, the state in which cells are not reacting can be measured accurately. Also, by lowering the liquid level of the culture to a predetermined liquid level when replacing a medium with a reagent solution, dilution of the reagent which is introduced afterwards is suppressed, and natural reaction of a cell that is to be a target sample can be obtained accurately. Further, emission intensity of the cells can be improved with a little amount of reagent. Further, when the liquid surface of the reagent is low, the liquid level varies in the vicinity of the securing member 121 of the liquid retaining section 129 due to an influence such as surface tension, but by keeping the liquid level of the liquid for search at a predetermined level during reaction of the microparticles, the state of microparticles during reaction can be measured accurately at all positions on the measurement chip 60. Further, by draining almost all reagent on the measurement chip 60 and thereafter introducing and draining the reagent, accuracy and efficiency of the cleaning of the measurement chip 60 can be improved.

In the foregoing, an apparatus and a screening method according to the present embodiment were described, but the present disclosure is not limited to the embodiment described above, and various variation and modification are conceivable based on a technical idea of the present disclosure.

For example, in the aforementioned embodiment, the liquid level is controlled in each of the first measurement step, the second measurement step and the cleaning step, but, it is not limited thereto, and the liquid level on the measurement chip 60 may be controlled in at least the second measurement step among the first measurement step, the second measurement step and the cleaning step. An effect similar to the above effect can be achieved by such a control.

Further, in the aforementioned embodiment, a culture medium was used as the reference liquid and a reagent solution was used as the liquid for searching, a but the reference liquid and the liquid for searching may be of the same type, or two kinds of liquids of other different combinations may be used. Particularly, liquids of the same type may be used as the reference liquid and the liquid for searching when sorting a microparticle, which is not emitting light by a reagent solution, but already emitting fluorescence without a reagent solution.

Figure 13A:
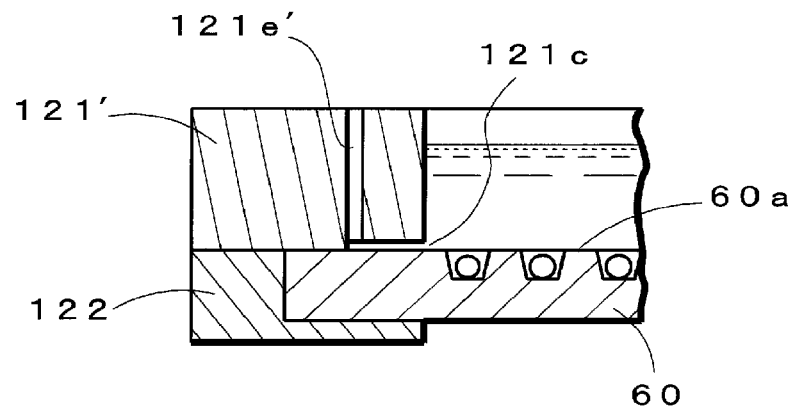
FIG. 13A is a partial cross-sectional view of a variant of the securing member shown in FIGS. 9A and 9B.
Figure 13B:
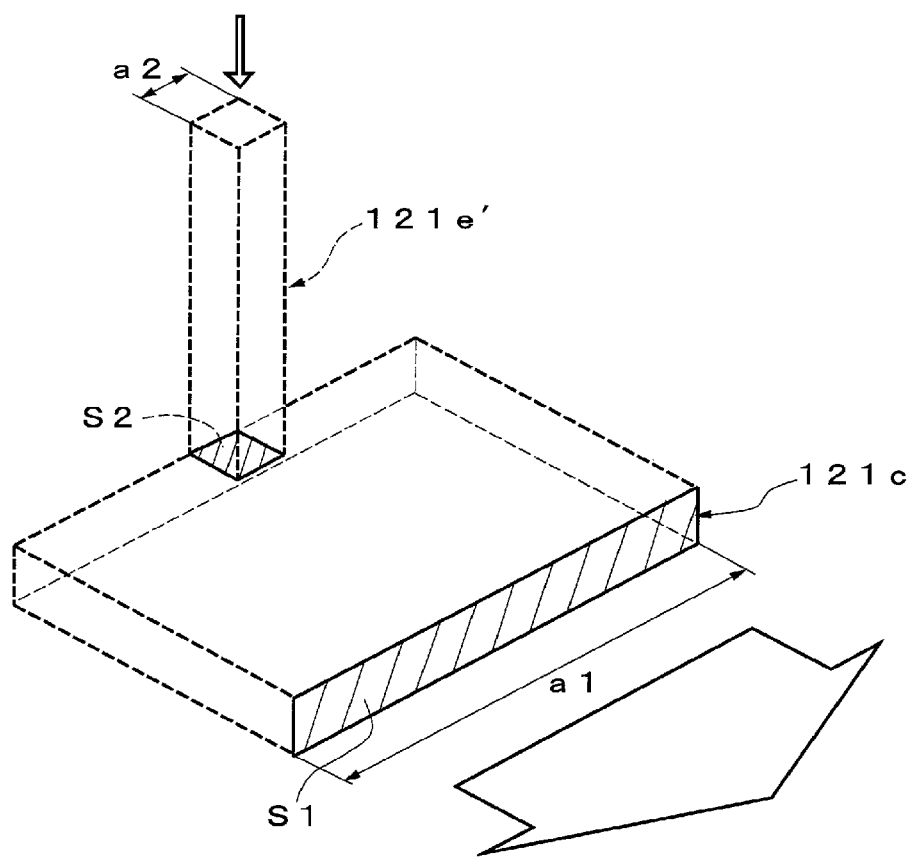
FIG. 13B is a schematic diagram showing a dimensional relationship between an introduction port and a flow channel in the securing member shown in FIG. 13A.

Also, in the aforementioned embodiment, the securing member 120 is provided with a buffer 121d (FIGS. 9A and 9B), but it is not limited thereto, and the securing member need not be provided with a buffer as shown in FIG. 13A. Specifically, a securing member 121' has an introduction port 121c, and a flow channel 121e' which extends in a substantially vertical direction and supplies a liquid to the introduction port from above the introduction port. Here, the size of the introduction port 121c and the flow channel 121e' is specified as a relationship as shown in FIG. 13B. That is, the following relationship holds:

$S1 < S2$, and $a1 > a2$, where

S1 is an area of a cross section in a longitudinal direction of the introduction port 121c, a1 is a width of the cross section of the introduction port 121c, S2 is an area of a cross section of the first flow channel 121e', and a2 is a width of the cross section of the first flow channel 121e'.

In this manner, by supplying the liquid to the introduction port 121c from above through the flow channel 121e' formed in a substantially vertical direction, and particularly by specifying the sizes of the introduction port and the flow channel to satisfy the aforementioned inequality, an effect of the present disclosure can be achieved.

Figure 14A:
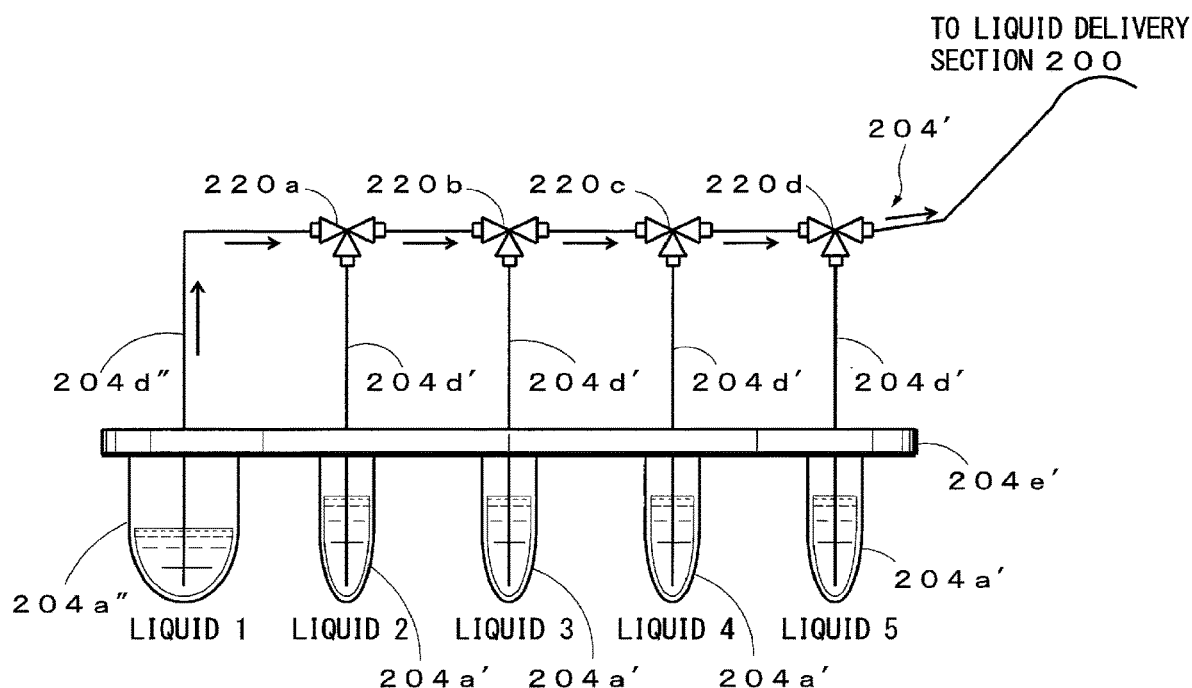
FIG. 14A is a diagram showing a variant of a liquid switchover section and a first liquid delivering section shown in FIG. 8, specifically showing how a reference liquid is delivered.
Figure 14B:
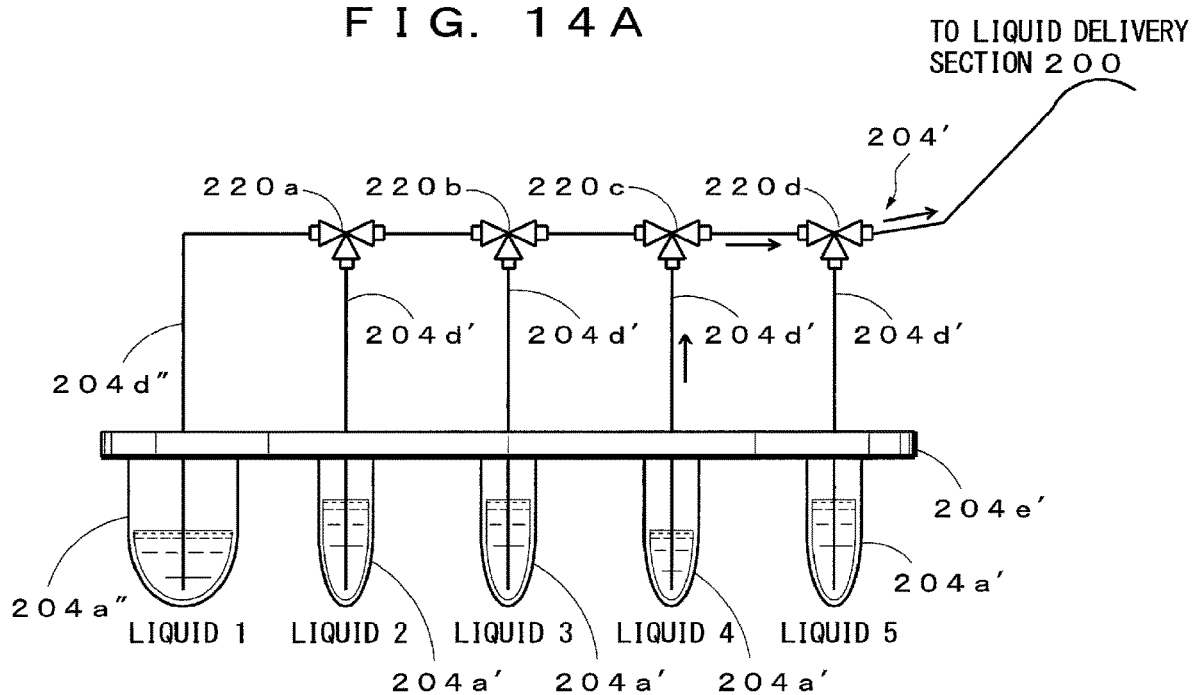
FIG. 14B is a diagram showing a variant of a liquid switchover section and a first liquid delivering section shown in FIG. 8, specifically showing how a next liquid is delivered.

Also, in the aforementioned embodiment, a revolver-type liquid switchover section 204 is provided, but it is not limited thereto, and a liquid as desired may be sent out to the liquid delivering section 202 using a solenoid valve such as a three-way valve as shown in FIGS. 14A and 14B. Specifically, a liquid switchover section 204' may have a holder 204e' that secures a plurality of test tube 204a' in which various liquids are contained, tubes 204d' connected to the plurality of test tubes, respectively, and electromagnetic 3-way valves 220a to 220d attached downstream of the tubes 204d'. In this variant embodiment, four electromagnetic 3-way valves 220a are 220d are arranged in a single row, with a test tube 204a" in which a culture medium that is to be the reference liquid is contained being attached to an electromagnetic 3-way valve 220a located at one end through a tube 204d", and an electromagnetic 3-way valve 220d located at the other end being connected to the liquid delivering section 202. The electromagnetic 3-way valves 220a to 220d are electrically connected to the control unit 203 or other control units, not shown, respectively, and, the valves are capable of being switched in response to a signal from the control unit 203. For example, with all of the electromagnetic 3-way valves 220a to 220d being in an open state first, only a culture medium (liquid 1) in test tube 204a" is supplied to the liquid delivering section 202 (FIG. 14A). Then, only the electromagnetic 3-way valve 220c is brought to a closed state to block the flow channel of the culture medium and supply a reagent solution (liquid 4) to the liquid delivering section 202 (FIG. 14B). By controlling open/close of the electromagnetic 3-way valves 220a to 220d individually in this manner, a desired liquid can be sent out to the liquid delivering section 202 with a predetermined timing.

Figure 15:
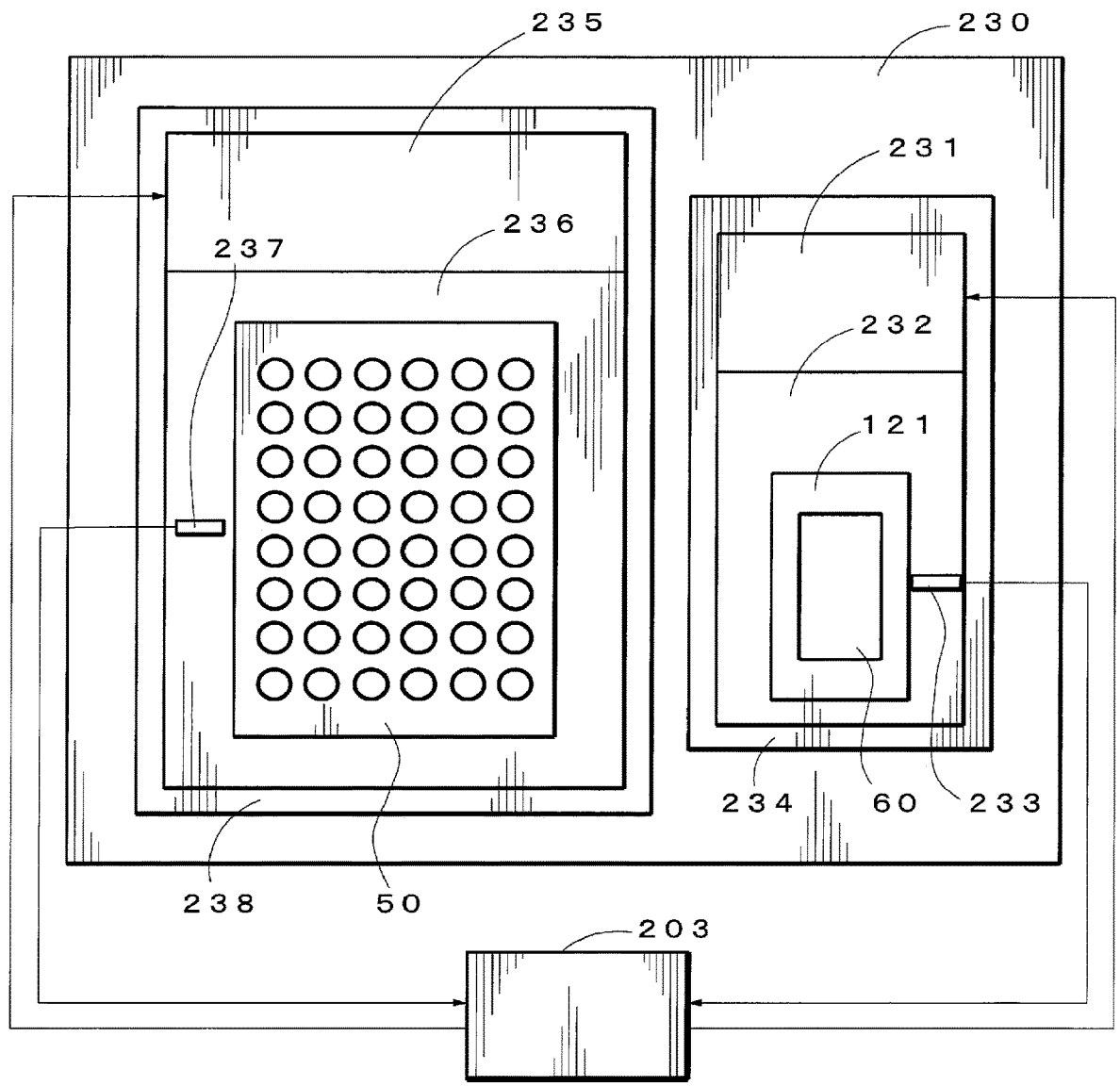
FIG. 15 is a diagram showing a variant in which a temperature controlling mechanism is mounted on a mounting table shown in FIG. 4.

Also, in a case where the target sample is a cell, the cell is substantially activated at around 37 degrees, and comes to a dormant state at around 4 degrees. Therefore, in order to keep a cell that is to be the sample at its optimum in accordance with the purpose, it is required to appropriately manage the temperature of the culture medium or the reagent. Thus, it is preferable that a mounting table on which the measurement chip 60 and the receiving plate 50 is placed is provided with a temperature controlling mechanism as shown in FIG. 15.

Specifically, the mounting table 230 has a cold heat source 231 such as a Peltier element that heats and cools the measurement chip 60, a heat transferring section 232 that has an opening configured to accommodate a securing member and transfers heat between the cold heat source 231 and the securing member 121, a temperature sensor 233 that is attached to the heat transferring section, and a heat insulating portion 234 that is disposed to cover both the cold heat source 231 and the heat transferring section 232. Also, the mounting table 230 has a cold heat source 235 that heats and cools the receiving plate 50, a heat transferring section 236 that is configured to accommodate the receiving plate 50 and transfers heat between the cold heat source 235 and the receiving plate 50, a temperature sensor 237 attached to the heat transferring section, and a heat insulating portion 238 that is disposed to cover both the cold heat source 235 and the heat transferring section 236. The cold heat source 231 and the temperature sensor 233 are connected to the control unit 203 or other control units, not shown, respectively. The control unit 203 heats and cools the cold heat source 231 based on a temperature measured with a temperature sensor 233. The cold heat source 235 comprises, for example, a Peltier element, and the heat transferring sections 232 and 236 are formed, for example, with iron, aluminum or copper or an alloy thereof.

With such a temperature controlling mechanism, the liquid in the liquid retaining section 129 or the well 61 in the measurement chip 60 can be kept at a desired temperature for the entire period of the sorting step, and thus the cell in the measurement chip 60 can be always kept optimum. Also, the cold heat source 235 and the temperature sensor 237 are similarly connected to the control unit 203 or other control units, not shown, and the cold heat source 235 is heated or cooled in accordance with the temperature measured with the temperature sensor 237. Accordingly, the liquid stored in the well 51 of the receiving plate 50 can be kept at a desired temperature for an entire period of the sorting step, and thus, the cell in the well 51 can be activated or made dormant, and the cell can be kept optimum depending on the purpose.

Note that, the variant embodiments described above include both a temperature controlling mechanism for the measurement chip 60 and a temperature controlling mechanism for the receiving plate 50, but only one of the temperature controlling mechanisms may be provided.

Figure 16:
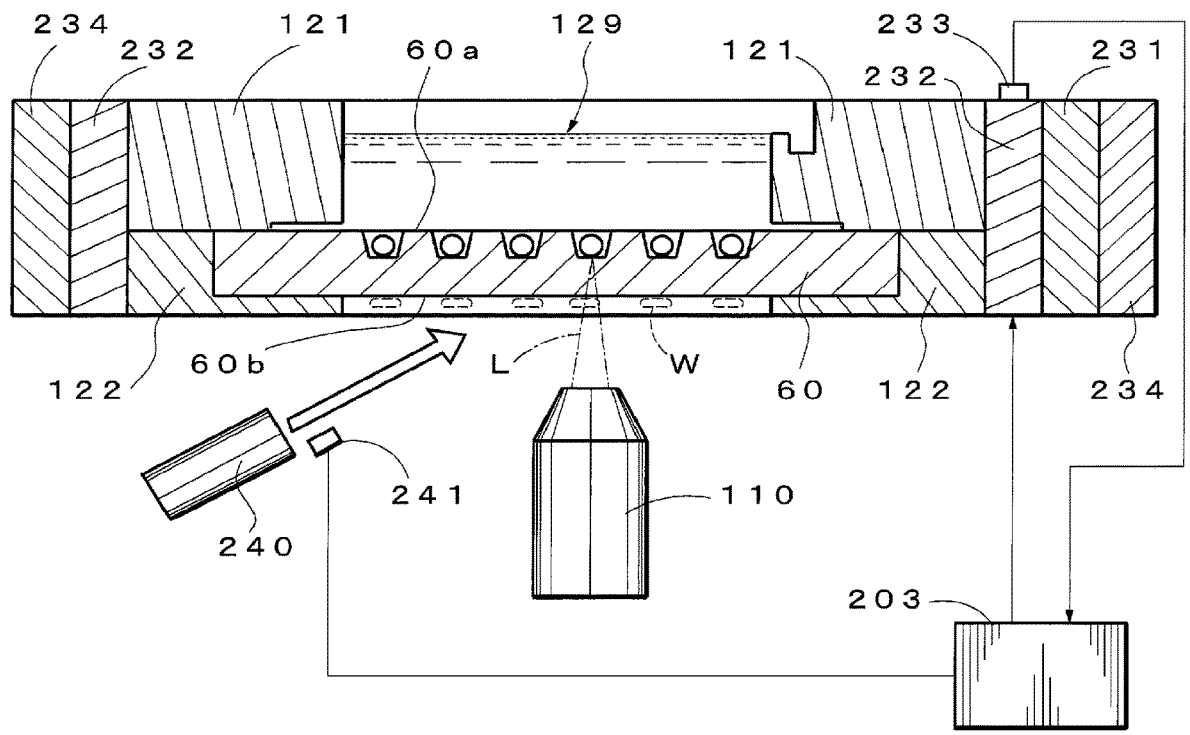
FIG. 16 is a diagram showing a variant in which a blower mechanism is provided below the mounting table.

Also, in a case where the mounting table 230 is provided with the temperature controlling mechanism for the measurement chip 60 and the temperature of the measurement chip 60 is controlled to be around 4° C. to make the cell dormant, condensation may occur on a lower face of the measurement chip 60. Thus, as shown in FIG. 16, a blower 240 may be disposed below the mounting table, and a gas may be blown on a lower face 60b of the measurement chip 60 that opposite to the face 60a on which the wells 61 are formed. Thereby, water droplets W due to condensation are not produced on the lower face 60b of the measurement chip 60, and water droplets W which have attached to the lower face 60b can be removed. Therefore, when light L from the objective lens 110 side is irradiated on a microparticle on the measurement chip 60, refraction and scattering of light due to the condensation can be prevented and optical information of the cell can be acquired accurately.

Further, a temperature sensor 241 that measures the temperature of gas discharged from the blower 240 may be provided. In this case, a signal from the temperature sensor 241 is received by the control unit 203 or other control units, and, the cold heat source 231 can be heated or cooled in accordance with the temperature of gas measured with the temperature sensor 241. Thereby, occurrence of the condensation on the lower face 60b of measurement chip 60 can be positively prevented, and also water droplets W due to condensation can be removed as soon as possible. More specifically, for example, in a case where the difference between the temperature of gas measured with the temperature sensor 241 and the temperature measured with the temperature sensor 233 is great, the difference between the temperature of the measurement chip 60 and the temperature measured with the temperature sensor 233 is also great, and thus, the preset temperature of the temperature sensor 233 offset in accordance with the temperature of gas measured with the temperature sensor 241, and the temperature (temperature of the cell in the well 61) on the measurement chip 60 can be set at a desired value.

Further, since the blower 240 is configured to selectively discharge warm air or cold air, it is possible to suppress fluctuation in control due to an ambient temperature change, and it is possible to accurately control the temperature of the measurement chip 60 and the receiving plate 50. Also, by using the blower and the cold heat source together, heat can be transferred to the measurement chip 60 and the collection plate 50 by both conduction and convection, and thus, and stable temperature control can be performed. Particularly, by accurately controlling the temperature of the measurement chip 60, fluctuation due to a difference in activity of the cell is suppressed, and an improved sorting accuracy can be maintained even if it is a different sample.

Note that, in the aforementioned variant embodiment, the cold heat source 231 is heated or cooled in accordance with the temperature measured with the temperature sensor 241, but it is not limited thereto, and one or both of the cold heat sources 231 and 235 may be heated or cooled. Also, in the aforementioned variant embodiment, both the heat source 231 and the blower 240 are provided, but it is not limited thereto, and only the blower 240 may be installed. Since either warm air or cold air can be selectively discharged from the blower 240, the blower 240 serves as a temperature controlling mechanism that can control the temperature of the measurement chip 60 and the liquid retaining section 129, and in addition, during the cooling, capable of preventing occurrence of condensation on the lower face 60b of the measurement chip 60.

Figure 17:
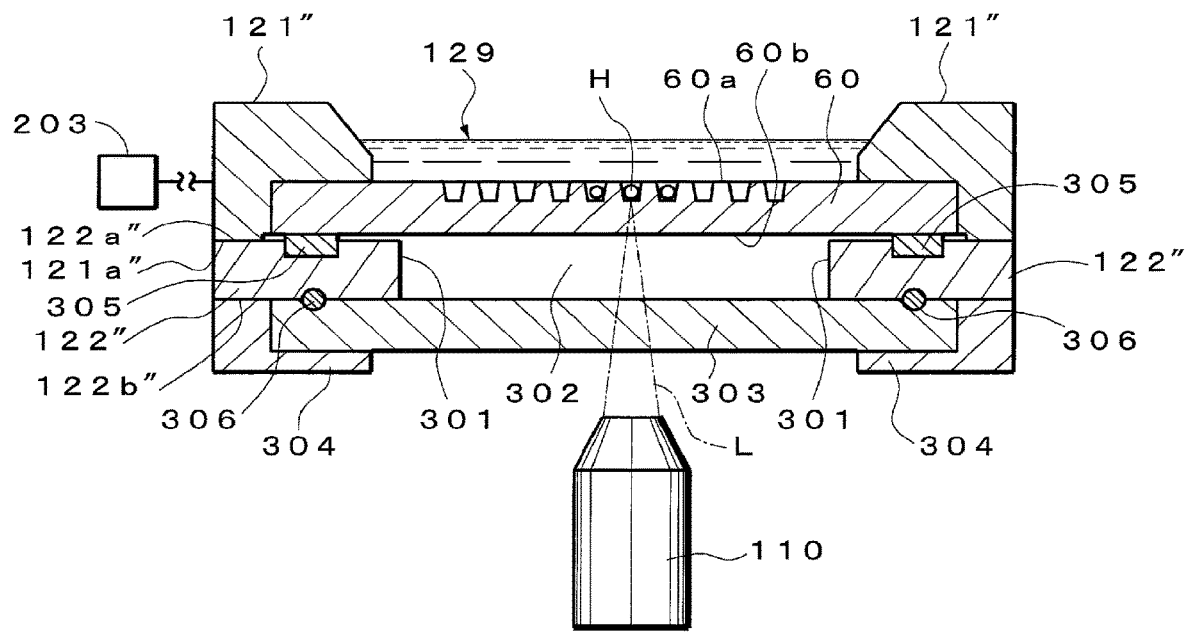
FIG. 17 is a diagram showing a variant of the securing member shown in FIG. 16.

Also, in order to prevent water droplets W from attaching the lower face 60b of measurement chip 60, in addition to the configuration in FIG. 16, it is also possible to provide a configuration in FIG. 17. Note that the configuration shown in FIG. 17 is basically the same as the configuration shown in FIG. 16, and same features are labelled with the same reference numerals, and different parts will be described below.

Specifically, the screening apparatus is provided with a securing member 121" that is a frame structure disposed on an upper face 60a side of the measurement chip 60, a securing member 122" that is a frame structure disposed on a lower face 60b side of the measurement chip 60, a plate-like member 303 formed of a light permeable material, the plate-like member being disposed on a lower face side of the securing member 122" such that an internal space 302 defined by a lower face 60b of the measurement chip 60 and an inner end face 301 of the securing member 122" is sealed, and a pressing member 304 that is a frame structure having a substantially L-shaped cross section and disposed at a lower face of the plate-like member and secures the plate-like member 303 to the securing member 122" and also secures the measurement chip 60 to a main body of the apparatus.

A securing member 121" is a member having a substantially reverse L-shaped cross section, and its lower face 121a" is in contact with an upper face 122a" of the securing member 122" to form a contact face at which heat can be transferred between the securing member 121" and the securing member 122". The securing member 122" is formed of a material having a thermal conductivity that is higher than that of the measurement chip 60, and, for example, with a metal which is the same as the securing member 121". The securing members 121" and 122" are formed, for example, of iron, aluminum or copper, or an alloy thereof. Accordingly, both of the securing members 121" and 122" are temperature controllable by the control unit 203 via a cold heat source and heat transferring section, not shown.

Between the securing member 122" and the measurement chip 60, a sealing member 305 having a substantially rectangular cross section is provided that seals between the upper face 122a" of the securing member 122" and the lower face 60b of the measurement chip 60. Between the securing member 122" and the plate-like member 303, a sealing member 306 having a substantially circular cross section is provided that seals between the lower face 122b" of the securing member 122" and the upper face 304a of the plate-like member 302. By the sealing members 305 and 306, the internal space 302 is sealed and isolated from outside air.

The plate-like member 303 is formed of, for example, a glass material such as quartz glass or borosilicate glass, or resin having a high optical-transparency such as acrylic resin, polystyrene and the like. During the screening, light irradiated from below penetrates the plate-like member 303 and arrives at microparticles M stored in wells in the measurement chip 60, and the reflected light or fluorescence also penetrates the plate-like member 303 and condensed on the objective lens 110. However, since the plate-like member 303 has a high optical transparency to an extent that does not to affect the screening accuracy, good measurement and collection can be achieved even in this configuration in which the plate-like member 303 is disposed on an optical path.

In this manner, by placing the plate-like member 303 below the measurement chip 60, and providing an internal space 302 in a sealed state between the measurement chip 60 and the plate-like member 303, the lower face 60b of the measurement chip 60 does not touch an outside air and the condensation can be prevented from occurring on the lower face 60b during the cooling. Also, the internal space 302 serves as a heat insulating layer and the measurement chip 60 can be insulated from outside air, and the temperature control of the measurement chip 60 and the liquid retaining section 129 can be facilitated.

During the screening, the measurement chip 60 is replaced with a new measurement chip at a predetermined timing, and thus, due to an influence of humidity of the outside space, air including moisture will be anavoidably introduced into the internal space 302. Therefore, even if the internal space 302 is sealed, condensation may be slightly produced at an inner end face 301 of the securing member 122", and when a water droplet exists on an optical path between the objective lens 110 and a microparticle in the well in a viewing region on the measurement chip 60, it could cause a decrease in the accuracy of measurement.

Thus, as shown in FIG. 18A, it may be configured such that an area S3 of an upper face 303a of a plate-like member 303 that is in contact with the internal space 302 is greater than an upper opening area S4 in the frame structure of the securing member 310 (S3>S4). For example, a lower end portion of an inner end face 311 of the securing member 310 is provided with a chamfered portion 312. By providing the chamfered portion 312, a groove portion 313 is formed between the securing member 310 and the plate-like member 303. Since the securing member 310 is formed of a material having a higher thermal conductivity than the measurement chip 60 or the plate-like member 303, the temperature of the securing member 310 decreases the most during the operating period. Accordingly, when condensation occurs in the internal space 302, it is produced at the securing member 310. In a case where condensation occurs on the inner end face 311 of the securing member 310 (FIG. 18B), a water droplet W' moves downward due to gravity and the water droplet W' enters into the groove portion 313 and is held therein (FIG. 18C). The chamfered portion 312 may be C-chamfering as shown in FIGS. 18A to 18C or may be R-chamfering. Further, in order to promote the holding and the collecting of the water droplet at the groove portion 313 by surface tension, it is preferable for the groove portion 313 to have a configuration that is tapered towards an outward direction in a vertical direction cross section.

In this manner, by providing a groove portion 313, in which water droplets are accumulated, outwardly of the inner end face 311 when in a plan arrow view of the securing member 310, water droplets W' can be removed from the viewing region (aperture area S4) on the measurement chip 60, and a good measurement accuracy can be maintained.

Figure 19:
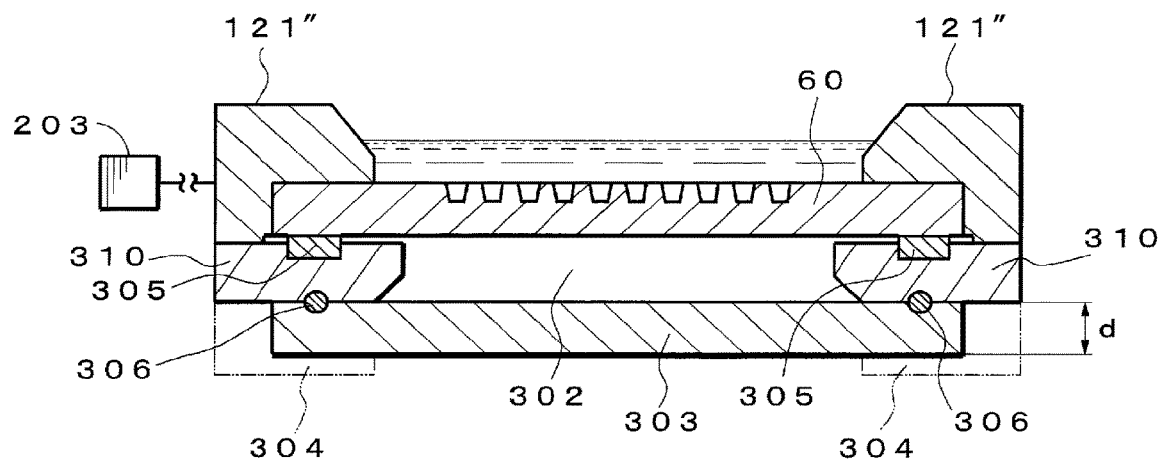
FIG. 19 is a diagram for explaining a thickness d of the plate-like member shown in FIGS. 18A to 18C.
Figure 20:
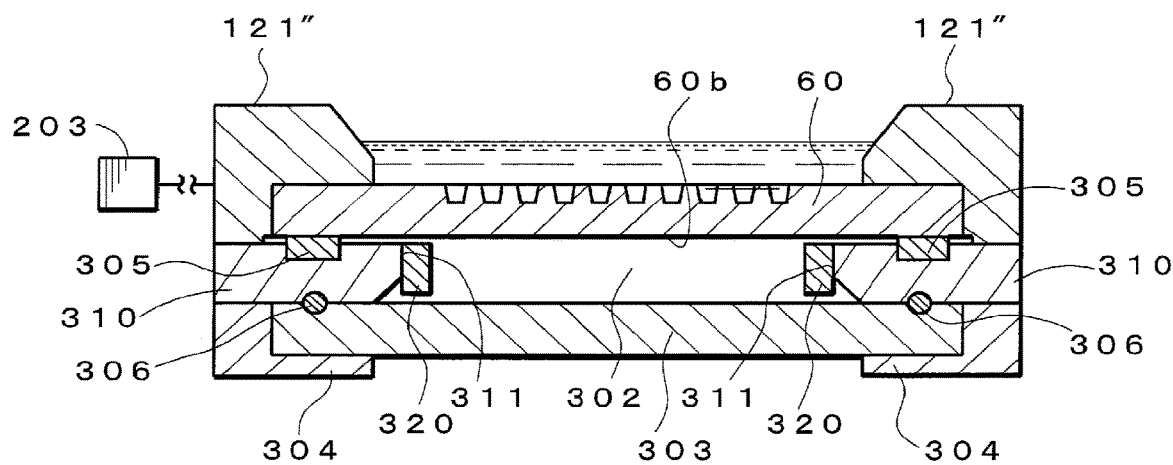
FIG. 20 is a diagram showing a variant of the configuration shown in FIGS. 18A to 18C, further provided with a moisture absorbing member.
Figure 21:
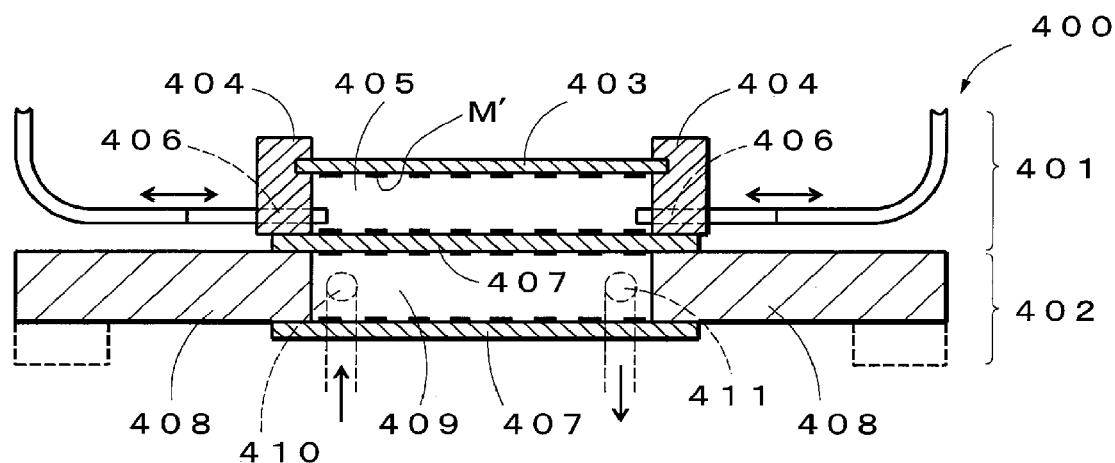
FIG. 21 is a schematic diagram showing a culture chamber for culturing cells used as samples of the related art.
Figure 22:
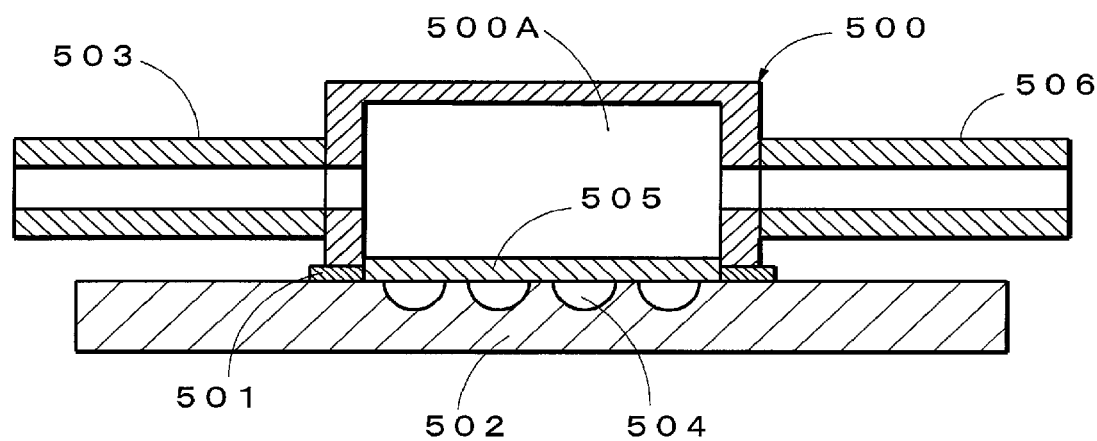
FIG. 22 is a cross sectional view showing another culture vessel of the related art.

Also, as has been described above, with the present screening apparatus, since luminance analysis or the like is performed based on light penetrating the plate-like member 303, defocus may occur between the objective lens 110 and the microparticle in the vertical direction depending on the thickness of the plate-like member 303. Thus, as shown in FIG. 19, it is preferable for thickness d of the plate-like member 303 to be constant at least in the aforementioned viewing region, and specifically, it is preferable that the dispersion of thickness d of the plate-like member 303 is less than or equal to 0.01 mm. With the dispersion of the thickness d being less than or equal to 0.01 mm, an amount of defocus in the vertical direction can be suppressed and an accuracy of measurement and collection can be improved.

Further, a moisture absorbing member 320 can be placed at an inner end face 311 of the securing member 310. The moisture absorbing member 320 is composed of a material that is capable of absorbing water, and for example, porous or fibrous material or desiccant such as silica gel and calcium chloride can be used. The moisture absorbing member 320 is provided such that its width dimension inward from the inner end face 311 decreases so as not to affect the viewing region in the measurement chip 60. Also, the moisture absorbing member 320 may be placed at an entirety of the inner end face 311, in other words, in a ring-like shape, or may be placed at a part of the inner end face 311, in a plan arrow view of the securing member 310. In this manner, by placing the moisture absorbing member 320 in the internal space 302, moisture in the internal space can be absorbed and occurrence of condensation on the lower face 60b or the inner end face 311 can be positively prevented.

What is claimed is:

1. A screening apparatus for searching for a predetermined microparticle based on optical information emitted from microparticles to selectively pick up the microparticle searched for, the screening apparatus comprising:
a measurement chip that is made of a light permeable material, the measurement chip having a well formed in or on an upper surface thereof, the well retaining a liquid including at least one of the microparticles;
a measuring section that is configured to acquire optical information emitted by the at least one of the microparticles retained in the well of the measurement chip;
an analyzing section that is configured to analyze the optical information to extract optical information associated with the at least one of the microparticles retained in the well;
a liquid retaining section provided on the measurement chip;
a draining section that is configured to drain a liquid retained in the liquid retaining section;
an introducing section that introduces a liquid into the liquid retaining section; and
a liquid level controlling section that controls a liquid level of the liquid retaining section.

2. The screening apparatus according to claim 1, wherein the liquid level controlling section separately controls an amount and a draining timing of a liquid drained from the liquid retaining section and an amount and an introducing timing of a liquid introduced into the liquid retaining section.

3. The screening apparatus according to claim 2, wherein the liquid level controlling section has a first liquid delivering section disposed downstream of the draining section, a second liquid delivering section disposed upstream of the introducing section and a control unit that controls operations of the first liquid delivering section and the second liquid delivering section.

4. The screening apparatus according to claim 1, further comprising a securing member that secures the measurement chip to a main body of the apparatus, the securing member being a frame structure disposed on an upper face of an edge portion of the measurement chip,
wherein the liquid retaining section is formed in an internal space of the securing member.

5. The screening apparatus according to claim 4, wherein the securing member has an introduction port formed between a lower face of the securing member and an upper face of the measurement chip, the introduction port extending in a direction of a plane of the measurement chip and having a flattened shape, and a first flow channel through which a liquid is supplied to the introduction port from above the introduction port, and
the introducing section includes the first flow channel and the introduction port.

6. The screening apparatus according to claim 5, wherein:

$S1<S2$, and $a1>a2$, where
S1 is an area of a cross section in a longitudinal direction of the introduction port,
a1 is a width of the cross section of the introduction port,
S2 is an area of a cross section of the first flow channel, and
a2 is a width of the cross section of the first flow channel.

7. The screening apparatus according to claim 4, wherein the securing member has a first draining port provided between a lower face of the securing member and an upper face of the measurement chip and second flow channel that is configured to drain a liquid to an outside through the first draining port, and
the draining section includes the first draining port and the second flow channel.

8. The screening apparatus according to claim 4, wherein the securing member has a first draining port provided between a lower face of the securing member and an upper face of the measurement chip, a second flow channel that is configured to drain a liquid to an outside through the first draining port, a second draining port provided above the first draining port, and a third flow channel that is configured to drain a liquid to an outside through the second draining port, and the draining section includes the first draining port, the second flow channel, the second draining port and the third flow channel.

9. The screening apparatus according to claim 8, wherein the securing member further has a dam section provided in the vicinity of the second draining port.

10. The screening apparatus of claim 1, wherein
a reference liquid is introduced on the measurement chip to measure position coordinate information of a well in the measurement chip, and thereafter the reference liquid is drained,
a liquid for searching on the measurement chip and measuring optical information emitted by microparticles in the well is introduced,
the liquid for searching on the measurement chip is drained,
the reference liquid is introduced and drained at least once to clean the measurement chip,
a microparticle which satisfied a predetermined collecting condition as a target sample based on the position coordinate information and the optical information thus measured is identified,
the target sample is collected, and
a liquid level on the measurement chip is controlled during, at least during the introduction for the liquid for searching.

11. The screening apparatus according to claim 10, wherein liquid for searching is introduced after the liquid surface of the reference liquid is lowered before the liquid for searching is replaced.

12. The screening apparatus according to claim 11, wherein the introduced reference liquid on the measurement chip includes a liquid level that is controlled to come to a first liquid level, and thereafter the reference liquid is drained such that the liquid surface is controlled to come to a second liquid level located directly above the well.

13. The screening apparatus according to claim 11, wherein the liquid surface is controlled to come to a third liquid level during the introduction of the liquid for searching.

14. The screening apparatus according to claim 11, wherein the liquid surface is controlled to come to a fourth liquid level during the draining of the liquid for searching.

15. The screening apparatus according to claim 14, wherein the fourth liquid level is set lower than the second liquid level.

16. The screening apparatus of claim 1, wherein the liquid retaining section is uncovered such that the liquid retaining section is not encapsulated or sealed.

17. A screening apparatus for searching for a predetermined microparticle based on optical information emitted from microparticles to selectively pick up the microparticle searched for, the screening apparatus comprising:
a measurement chip that is made of a light permeable material, the measurement chip having a well formed in or on an upper surface thereof, the well retaining a liquid including at least one of the microparticles;
a measuring section that is configured to acquire optical information emitted by the at least one of the microparticles retained in the well of the measurement chip;
an analyzing section that is configured to analyze the optical information to extract optical information associated with the at least one of the microparticles retained in the well;
a temperature controlling section configured to control a temperature of the measurement chip and/or the receiving plate;
a securing member that secures the measurement chip to a main body of the apparatus, the securing member being a frame structure disposed on a lower face of the measurement chip; and
a plate-like member formed of a light permeable material, the plate-like member being disposed on a lower face side of the securing member to seal an internal space defined by a lower face of the measurement chip and an inner end face of the securing member.

* * * * *